United States Patent
Uno et al.

(10) Patent No.: US 8,044,019 B2
(45) Date of Patent: Oct. 25, 2011

(54) CELL PENETRATING PEPTIDE

(75) Inventors: Shusei Uno, Osaka (JP); Kaeko Kamide, Osaka (JP); Hiroshi Nakakubo, Osaka (JP)

(73) Assignee: Mitsubishi Tanabe Pharma Corporation, Osaka-shi (JP)

(*) Notice: Subject to any disclaimer, the term of this patent is extended or adjusted under 35 U.S.C. 154(b) by 520 days.

(21) Appl. No.: 12/091,807

(22) PCT Filed: Oct. 27, 2006

(86) PCT No.: PCT/JP2006/321465
§ 371 (c)(1),
(2), (4) Date: Apr. 28, 2008

(87) PCT Pub. No.: WO2007/049731
PCT Pub. Date: May 3, 2007

(65) Prior Publication Data
US 2010/0048487 A1    Feb. 25, 2010

(30) Foreign Application Priority Data
Oct. 28, 2005    (JP) .................................. 2005-314355

(51) Int. Cl.
*A61K 38/10* (2006.01)
*C07K 7/08* (2006.01)
(52) U.S. Cl. ......... 514/1.2; 514/21.5; 530/326; 530/345
(58) Field of Classification Search .................. None
See application file for complete search history.

(56) References Cited

U.S. PATENT DOCUMENTS
2004/0034888 A1   2/2004   Liu et al.

FOREIGN PATENT DOCUMENTS
| JP | 2003-252802 | | 9/2003 |
| WO | WO 98/20016 | | 5/1998 |
| WO | WO 9846750 A1 | * | 10/1998 |
| WO | WO 02/18572 A2 | | 3/2002 |
| WO | WO 03/097671 A1 | | 11/2003 |

OTHER PUBLICATIONS

Shiro Niki, et al., "Maku Toka Peptide o Mochiita Tanpakushitsu Saibonai Iso", Kagaku to Seibutsu, vol. 43, No. 10, Oct. 1, 2005, pp. 649-653.

Kenji Kono, et al., "Saibo no Naka eno Chokkobin-Maku Toka Peptide o Hyomei ni Motsu", Ribosome Chemical, vol. 57, No. 6, 2002, pp. 51-52.

Thomas Plénat, et al., "Interaction of Primary Amphipathic Cell-Penetrating Peptides with Phospholipid-Supported Monolayers", Langmuir, vol. 20, No. 21, 2004, pp. 9255-9261.

Yousuke Nishio, et al, "Comparative Complete Genome Sequence Analysis of the Amino Acid Replacements Responsible for the Thermostability of *Corynebacterium efficiens*", Genome Research, vol. 13, 2003, pp. 1572-1579.

(Continued)

*Primary Examiner* — Jeffrey E Russel
(74) *Attorney, Agent, or Firm* — Oblon, Spivak, McClelland, Maier & Neustadt, L.L.P.

(57) ABSTRACT

According to the present invention, it is possible to provide a novel cell penetrating peptide that transports proteins into cells and/or into nuclei at higher frequency than conventional cell penetrating peptides, and a pharmaceutical containing the peptide.

31 Claims, 21 Drawing Sheets

OTHER PUBLICATIONS

Satoshi Ōmura, et al., "Genome sequence of an industrial microorganism *Streptomyces avermitlis*: Deducing the ability of producing secondary metabolites", Proc. Natl. Acad. Sci. USA, vol. 98, No. 21, 2001, pp. 12215-12220.

F. O. Glöckner, et al., "Complete genome sequence of the marine planctomycete *Pirellula* sp. Strain 1", Proc. Natl. Acad. Sci. USA, vol. 100, No. 14, 2003, pp. 8298-8303.

Olivier Jaillon, et al., "Genome duplication in the teleost fish Tetraodon nigroviridis reveals the early vertebrate proto-karyotype", Nature, vol. 431, 2004, pp. 946-957.

Tatyana V. Golovkina, et al., "A Novel Membrane Protien Is a Mouse Mammary Tumor Virus Receptor", Journal of Virology, vol. 72, No. 4, XP 002497675, Apr. 1998, pp. 3066-3071.

Kenji Kokura, et al., "The Ski-Binding Protien C184M Negatively Regulates Tumor Growth Factor-β Signaling by Sequestering the Smad Protiens in the Cytoplasm", The Journal of Biological Chemistry, vol. 278, No. 22, XP 002497676, May 2003, pp. 20133-20139.

Joaquin Royo, et al., "Characterzation of Three Potato Lipoxygenases with Distinct Enzymatic Activities and Different Organ-Specific and Wound-Regulated Expression Patterns", The Journal of Biological Chemistry, vol. 271, No. 35, XP 002186561, Aug. 30, 1996, pp. 21012-21019.

\* cited by examiner

TAT
(Positive)

KSH1

SEQUENCE LISTING

<160> NUMBER OF SEQ ID NOS: 121

<210> SEQ ID NO 1
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 1

Arg Leu Trp Met Arg Trp Tyr Ser Pro Thr Thr Arg Arg Tyr Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 2

Lys Leu Trp Met Arg Trp Tyr Ser Ala Thr Thr Arg Arg Tyr Gly
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 3

Lys Leu Trp Met Arg Trp Tyr Ser Pro Thr Thr Arg Ala Tyr Gly
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 4

Lys Leu Trp Met Arg Trp Trp Ser Pro Thr Thr Arg Arg Tyr Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 5

Arg Leu Trp Met Arg Trp Trp Ser Ala Thr Thr Arg Ala Tyr Gly
1               5                   10                  15

<210> SEQ ID NO 6
<211> LENGTH: 15
<212> TYPE: PRT
<213> ORGANISM: Artificial Sequence
<220> FEATURE:

<223> OTHER INFORMATION: Designed peptide to act as PTD(Protein
       Transduction Domain)

<400> SEQUENCE: 6

Lys Leu Ala Met Arg Ala Tyr Ser Pro Thr Thr Arg Arg Tyr Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Designed peptide to act as PTD(Protein
       Transduction Domain)

<400> SEQUENCE: 7

Lys Leu Trp Met Arg Trp Tyr Ser Pro Trp Thr Arg Arg Tyr Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Designed peptide to act as PTD(Protein
       Transduction Domain)

<400> SEQUENCE: 8

Arg Leu Trp Met Arg Trp Tyr Ser Pro Trp Thr Arg Arg Tyr Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Designed peptide to act as PTD(Protein
       Transduction Domain)

<400> SEQUENCE: 9

Arg Leu Trp Met Arg Trp Tyr Ser Pro Trp Thr Arg Arg Trp Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Designed peptide to act as PTD(Protein
       Transduction Domain)

<400> SEQUENCE: 10

Ala Leu Trp Met Arg Trp Tyr Ser Pro Thr Thr Arg Arg Tyr Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Designed peptide to act as PTD(Protein
       Transduction Domain)

<400> SEQUENCE: 11

Arg Ala Trp Met Arg Trp Tyr Ser Pro Thr Thr Arg Arg Tyr Gly
1               5                   10                  15

<210> SEQ ID NO 12

```
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 12

Arg Leu Ala Met Arg Trp Tyr Ser Pro Thr Thr Arg Arg Tyr Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 13

Arg Leu Trp Ala Arg Trp Tyr Ser Pro Thr Thr Arg Arg Tyr Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 14

Arg Leu Trp Met Ala Trp Tyr Ser Pro Thr Thr Arg Arg Tyr Gly
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 15

Arg Leu Trp Met Arg Ala Tyr Ser Pro Thr Thr Arg Arg Tyr Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 16

Arg Leu Trp Met Arg Trp Ala Ser Pro Thr Thr Arg Arg Tyr Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 17

Arg Leu Trp Met Arg Trp Tyr Ala Pro Thr Thr Arg Arg Tyr Gly
```

-continued

<210> SEQ ID NO 18
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 18

Arg Leu Trp Met Arg Trp Tyr Ser Gly Thr Thr Arg Arg Tyr Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 19

Arg Leu Trp Met Arg Trp Tyr Ser Pro Ala Thr Arg Arg Tyr Gly
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 20

Arg Leu Trp Met Arg Trp Tyr Ser Pro Thr Ala Arg Arg Tyr Gly
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 21

Arg Leu Trp Met Arg Trp Tyr Ser Pro Thr Thr Ala Arg Tyr Gly
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 22

Arg Leu Trp Met Arg Trp Tyr Ser Pro Thr Thr Arg Arg Ala Gly
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

-continued

<400> SEQUENCE: 23

Arg Leu Leu Met Arg Leu Tyr Ser Pro Thr Thr Arg Arg Tyr Gly
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 24

Arg Leu Phe Met Arg Phe Tyr Ser Pro Thr Thr Arg Arg Tyr Gly
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 25

Arg Leu Ile Met Arg Ile Tyr Ser Pro Thr Thr Arg Arg Tyr Gly
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 26

Arg Leu Trp Met Arg Trp Tyr Ala Pro Ala Ala Arg Arg Tyr Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 27

Arg Leu Ile Met Arg Ile Tyr Ala Pro Thr Thr Arg Arg Tyr Gly
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 28

Arg Leu Val Met Arg Val Tyr Ser Pro Thr Thr Arg Arg Tyr Gly
1               5                   10                  15

<210> SEQ ID NO 29
<211> LENGTH: 15
<212> TYPE: PRT

```
<213> ORGANISM: Artificial Sequence
<220> FEATURE:
<223> OTHER INFORMATION: Designed peptide to act as PTD(Protein
      Transduction Domain)

<400> SEQUENCE: 29

Arg Leu Tyr Met Arg Tyr Tyr Ser Pro Thr Thr Arg Arg Tyr Gly
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 30

Arg Leu Trp Met Arg Trp Tyr Ser Pro Arg Thr Arg Ala Tyr Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 31

Arg Leu Trp Met Arg Trp Tyr Ser Pro Thr Thr Arg Ala Arg Gly
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 32

Arg Leu Trp Met Arg Trp Tyr Ser Pro Thr Thr Arg Arg Tyr Ala
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 33

Lys Leu Trp Met Arg Trp Tyr Ser Pro Thr Thr Arg Arg Tyr Gly
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 34

Gly Tyr Arg Arg Thr Thr Pro Ser Tyr Trp Arg Met Trp Leu Arg
1               5                   10                  15
```

-continued

```
<210> SEQ ID NO 35
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 35

Ile Pro Ser Arg Trp Lys Asp Gln Phe Trp Lys Arg Trp His Tyr
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 36

Lys Asn Ala Trp Lys His Ser Ser Cys His His Arg His Gln Ile
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 37

Arg Val Arg Glu Trp Trp Tyr Thr Ile Thr Leu Lys Gln Glu Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 38

Leu Ile Thr Lys Gln Tyr Arg Tyr Pro Ser Arg Arg Arg Phe Asn
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 39

Gln Gln His Leu Leu Ile Ala Ile Asn Gly Tyr Pro Arg Tyr Asn
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 40
```

```
Gly Tyr Gly Asn Cys Arg His Phe Lys Gln Lys Pro Arg Arg Asp
1               5                   10                  15
```

<210> SEQ ID NO 41
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 41

```
Arg Thr Leu Val Asn Glu Tyr Lys Asn Thr Leu Lys Phe Ser Lys
1               5                   10                  15
```

<210> SEQ ID NO 42
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 42

```
Lys Arg Pro Thr Met Arg Phe Arg Tyr Thr Trp Asn Pro Met Lys
1               5                   10                  15
```

<210> SEQ ID NO 43
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 43

```
Trp Lys Cys Arg Arg Gln Cys Phe Arg Val Leu His His Trp Asn
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 44

```
Trp Lys Ala Arg Arg Gln Ala Phe Arg Val Leu His His Trp Asn
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 45

```
Trp Lys Trp Arg Arg Gln Trp Phe Arg Val Leu His His Trp Asn
1               5                   10                  15
```

<210> SEQ ID NO 46
<211> LENGTH: 15
<212> TYPE: PRT
<213> ORGANISM: Artificial Sequence
<220> FEATURE:

-continued

<223> OTHER INFORMATION: Designed peptide to act as PTD(Protein
      Transduction Domain)

<400> SEQUENCE: 46

Trp Lys Ala Arg Arg Gln Cys Phe Arg Val Leu His His Trp Asn
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 47

Trp Lys Cys Arg Arg Gln Ala Phe Arg Val Leu His His Trp Asn
1               5                   10                  15

<210> SEQ ID NO 48
<211> LENGTH: 45
<212> TYPE: DNA
<213> ORGANISM: Artificial Sequence
<220> FEATURE:
<223> OTHER INFORMATION: Designed sequence based on PTD(Protein
      Transduction Domain)
<220> FEATURE:
<221> NAME/KEY: misc_feature
<222> LOCATION: (6)..(6)
<223> OTHER INFORMATION: n stands for any base
<220> FEATURE:
<221> NAME/KEY: misc_feature
<222> LOCATION: (15)..(15)
<223> OTHER INFORMATION: n stands for any base
<220> FEATURE:
<221> NAME/KEY: misc_feature
<222> LOCATION: (24)..(24)
<223> OTHER INFORMATION: n stands for any base
<220> FEATURE:
<221> NAME/KEY: misc_feature
<222> LOCATION: (27)..(27)
<223> OTHER INFORMATION: n stands for any base
<220> FEATURE:
<221> NAME/KEY: misc_feature
<222> LOCATION: (30)..(30)
<223> OTHER INFORMATION: n stands for any base
<220> FEATURE:
<221> NAME/KEY: misc_feature
<222> LOCATION: (33)..(33)
<223> OTHER INFORMATION: n stands for any base
<220> FEATURE:
<221> NAME/KEY: misc_feature
<222> LOCATION: (36)..(36)
<223> OTHER INFORMATION: n stands for any base
<220> FEATURE:
<221> NAME/KEY: misc_feature
<222> LOCATION: (39)..(39)
<223> OTHER INFORMATION: n stands for any base
<220> FEATURE:
<221> NAME/KEY: misc_feature
<222> LOCATION: (45)..(45)
<223> OTHER INFORMATION: n stands for any base

<400> SEQUENCE: 48
aarytntgga tgmgntggta ywsnccnacn acnmgnmgnt ayggn          45

<210> SEQ ID NO 49
<211> LENGTH: 45
<212> TYPE: DNA
<213> ORGANISM: Artificial Sequence
<220> FEATURE:
<223> OTHER INFORMATION: Designed sequence based on PTD(Protein
      Transduction Domain)
<220> FEATURE:

```
<221> NAME/KEY: misc_feature
<222> LOCATION: (3)..(3)
<223> OTHER INFORMATION: n stands for any base
<220> FEATURE:
<221> NAME/KEY: misc_feature
<222> LOCATION: (9)..(9)
<223> OTHER INFORMATION: n stands for any base
<220> FEATURE:
<221> NAME/KEY: misc_feature
<222> LOCATION: (12)..(12)
<223> OTHER INFORMATION: n stands for any base
<220> FEATURE:
<221> NAME/KEY: misc_feature
<222> LOCATION: (15)..(15)
<223> OTHER INFORMATION: n stands for any base
<220> FEATURE:
<221> NAME/KEY: misc_feature
<222> LOCATION: (18)..(18)
<223> OTHER INFORMATION: n stands for any base
<220> FEATURE:
<221> NAME/KEY: misc_feature
<222> LOCATION: (21)..(21)
<223> OTHER INFORMATION: n stands for any base
<220> FEATURE:
<221> NAME/KEY: misc_feature
<222> LOCATION: (24)..(24)
<223> OTHER INFORMATION: n stands for any base
<220> FEATURE:
<221> NAME/KEY: misc_feature
<222> LOCATION: (33)..(33)
<223> OTHER INFORMATION: n stands for any base
<220> FEATURE:
<221> NAME/KEY: misc_feature
<222> LOCATION: (42)..(42)
<223> OTHER INFORMATION: n stands for any base

<400> SEQUENCE: 49
ggntaymgnm gnacnacncc nwsntaytgg mgnatgtggy tnaar          45

<210> SEQ ID NO 50
<211> LENGTH: 11
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 50

Tyr Gly Arg Lys Lys Arg Arg Gln Arg Arg Arg
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Designed peptide to act as PTD(Protein
      Transduction Domain)

<400> SEQUENCE: 51

Gly Arg Lys Lys Arg Arg Gln Pro Pro Gln
1               5                   10

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
gccatggtga gcaagggcga ggagctgttc          30
```

-continued

<210> SEQ ID NO 53
<211> LENGTH: 70
<212> TYPE: DNA
<213> ORGANISM: Artificial Sequence
<220> FEATURE:
<223> OTHER INFORMATION: primer

<400> SEQUENCE: 53
caccgcggcg acgttgtcgt cgtttcttcc tgccgtagga tcccccctccc ttgtacagct    60 cgtccatgcc                                                            70

<210> SEQ ID NO 54
<211> LENGTH: 69
<212> TYPE: DNA
<213> ORGANISM: Artificial Sequence
<220> FEATURE:
<223> OTHER INFORMATION: primer

<400> SEQUENCE: 54
cgctcagcgt cgactcaccc gtgatgatgg tggtgatgac tcgagccgcc accgcggcga    60
cgttgtcgt                                                             69

<210> SEQ ID NO 55
<211> LENGTH: 88
<212> TYPE: DNA
<213> ORGANISM: Artificial Sequence
<220> FEATURE:
<223> OTHER INFORMATION: primer

<400> SEQUENCE: 55
aagccatggg aggggggatcc tacggcagga agaaacgacg acaacgtcgc cgcggtggcg    60
gctcgagtat ggtgagcaag ggcgagga                                        88

<210> SEQ ID NO 56
<211> LENGTH: 72
<212> TYPE: DNA
<213> ORGANISM: Artificial Sequence
<220> FEATURE:
<223> OTHER INFORMATION: primer

<400> SEQUENCE: 56
ccgctcagcg tcgactcacc cgtgatgatg gtggtgatga gaaccaccac ccttgtacag    60
ctcgtccatg cc                                                         72

<210> SEQ ID NO 57
<211> LENGTH: 15
<212> TYPE: PRT
<213> ORGANISM: Artificial Sequence
<220> FEATURE:
<223> OTHER INFORMATION: Designed peptide to act as PTD(Protein
    Transduction Domain)

<400> SEQUENCE: 57

Tyr Asn Arg Thr Asn Arg Arg Gly Gln Ala Arg Lys Asp Asp Ser
1               5                   10                  15

<210> SEQ ID NO 58
<211> LENGTH: 59
<212> TYPE: DNA
<213> ORGANISM: Artificial Sequence
<220> FEATURE:
<223> OTHER INFORMATION: DNA for annealing

<400> SEQUENCE: 58
tcgagccgcc acctccgtat cgacgagtag ttggcgagta ccatcgcatc cacaacttg        59

<210> SEQ ID NO 59
<211> LENGTH: 59
<212> TYPE: DNA
<213> ORGANISM: Artificial Sequence
<220> FEATURE:
<223> OTHER INFORMATION: DNA for annealing

<400> SEQUENCE: 59
gatccaagtt gtggatgcga tggtactcgc caactactcg tcgatacgga ggtggcggc        59

<210> SEQ ID NO 60
<211> LENGTH: 59
<212> TYPE: DNA
<213> ORGANISM: Artificial Sequence
<220> FEATURE:
<223> OTHER INFORMATION: DNA for annealing

<400> SEQUENCE: 60
gatccaggtt gtggatgcga tggtactcgc caactactcg tcgatacgga ggtggcggc        59

<210> SEQ ID NO 61
<211> LENGTH: 59
<212> TYPE: DNA
<213> ORGANISM: Artificial Sequence
<220> FEATURE:
<223> OTHER INFORMATION: DNA for annealing

<400> SEQUENCE: 61
tcgagccgcc acctccgtat cgacgagtag ttggcgagta ccatcgcatc cacaacctg        59

<210> SEQ ID NO 62
<211> LENGTH: 59
<212> TYPE: DNA
<213> ORGANISM: Artificial Sequence
<220> FEATURE:
<223> OTHER INFORMATION: DNA for annealing

<400> SEQUENCE: 62
gatccaagtt gtggatgcga tggtactcgg caactactcg tcgatacgga ggtggcggc        59

<210> SEQ ID NO 63
<211> LENGTH: 59
<212> TYPE: DNA
<213> ORGANISM: Artificial Sequence
<220> FEATURE:
<223> OTHER INFORMATION: DNA for annealing

<400> SEQUENCE: 63
tcgagccgcc acctccgtat cgacgagtag ttgccgagta ccatcgcatc cacaacttg        59

<210> SEQ ID NO 64
<211> LENGTH: 59
<212> TYPE: DNA
<213> ORGANISM: Artificial Sequence
<220> FEATURE:
<223> OTHER INFORMATION: DNA for annealing

<400> SEQUENCE: 64
gatccaagtt gtggatgcga tggtactcgc caactactcg tgcatacgga ggtggcggc        59

<210> SEQ ID NO 65
<211> LENGTH: 59
<212> TYPE: DNA
<213> ORGANISM: Artificial Sequence
<220> FEATURE:

<223> OTHER INFORMATION: DNA for annealing

<400> SEQUENCE: 65
tcgagccgcc acctccgtat gcacgagtag ttggcgagta ccatcgcatc cacaacttg    59

<210> SEQ ID NO 66
<211> LENGTH: 59
<212> TYPE: DNA
<213> ORGANISM: Artificial Sequence
<220> FEATURE:
<223> OTHER INFORMATION: DNA for annealing

<400> SEQUENCE: 66
gatccaagtt gtggatgcga tggtggtcgc caactactcg tcgatacgga ggtggcggc    59

<210> SEQ ID NO 67
<211> LENGTH: 59
<212> TYPE: DNA
<213> ORGANISM: Artificial Sequence
<220> FEATURE:
<223> OTHER INFORMATION: DNA for annealing

<400> SEQUENCE: 67
tcgagccgcc acctccgtat cgacgagtag ttggcgacca ccatcgcatc cacaacttg    59

<210> SEQ ID NO 68
<211> LENGTH: 59
<212> TYPE: DNA
<213> ORGANISM: Artificial Sequence
<220> FEATURE:
<223> OTHER INFORMATION: DNA for annealing

<400> SEQUENCE: 68
tcgagccgcc acctccgtat gcacgagtag tggccgacca ccatcgcatc cacaacctg    59

<210> SEQ ID NO 69
<211> LENGTH: 59
<212> TYPE: DNA
<213> ORGANISM: Artificial Sequence
<220> FEATURE:
<223> OTHER INFORMATION: DNA for annealing

<400> SEQUENCE: 69
gatccaggtt gtggatgcga tggtggtcgg ccactactcg tgcatacgga ggtggcggc    59

<210> SEQ ID NO 70
<211> LENGTH: 59
<212> TYPE: DNA
<213> ORGANISM: Artificial Sequence
<220> FEATURE:
<223> OTHER INFORMATION: DNA for annealing

<400> SEQUENCE: 70
tcgagccgcc acctccgtat cgacgagtag ttggcgagta agctcgcata gccaacttg    59

<210> SEQ ID NO 71
<211> LENGTH: 59
<212> TYPE: DNA
<213> ORGANISM: Artificial Sequence
<220> FEATURE:
<223> OTHER INFORMATION: DNA for annealing

<400> SEQUENCE: 71
gatccaagtt ggctatgcga gcttactcgc caactactcg tcgatacgga ggtggcggc    59

<210> SEQ ID NO 72

-continued

<211> LENGTH: 59
<212> TYPE: DNA
<213> ORGANISM: Artificial Sequence
<220> FEATURE:
<223> OTHER INFORMATION: DNA for annealing

<400> SEQUENCE: 72
tcgagccgcc acctccgtat cgacgagtcc aaggcgagta ccatcgcatc cacaacttg    59

<210> SEQ ID NO 73
<211> LENGTH: 59
<212> TYPE: DNA
<213> ORGANISM: Artificial Sequence
<220> FEATURE:
<223> OTHER INFORMATION: DNA for annealing

<400> SEQUENCE: 73
gatccaagtt gtggatgcga tggtactcgc cttggactcg tcgatacgga ggtggcggc    59

<210> SEQ ID NO 74
<211> LENGTH: 59
<212> TYPE: DNA
<213> ORGANISM: Artificial Sequence
<220> FEATURE:
<223> OTHER INFORMATION: DNA for annealing

<400> SEQUENCE: 74
gatccaggtt gtggatgcga tggtactcgc cctggactcg tcgatacgga ggtggcggc    59

<210> SEQ ID NO 75
<211> LENGTH: 59
<212> TYPE: DNA
<213> ORGANISM: Artificial Sequence
<220> FEATURE:
<223> OTHER INFORMATION: DNA for annealing

<400> SEQUENCE: 75
tcgagccgcc acctccgtat cgacgagtcc agggcgagta ccatcgcatc cacaacctg    59

<210> SEQ ID NO 76
<211> LENGTH: 59
<212> TYPE: DNA
<213> ORGANISM: Artificial Sequence
<220> FEATURE:
<223> OTHER INFORMATION: DNA for annealing

<400> SEQUENCE: 76
gatccaggtt gtggatgcga tggtactcgc cctggactcg tcgatgggga ggtggcggc    59

<210> SEQ ID NO 77
<211> LENGTH: 59
<212> TYPE: DNA
<213> ORGANISM: Artificial Sequence
<220> FEATURE:
<223> OTHER INFORMATION: DNA for annealing

<400> SEQUENCE: 77
tcgagccgcc acctccccat cgacgagtcc agggcgagta ccatcgcatc cacaacctg    59

<210> SEQ ID NO 78
<211> LENGTH: 59
<212> TYPE: DNA
<213> ORGANISM: Artificial Sequence
<220> FEATURE:
<223> OTHER INFORMATION: DNA for annealing

<400> SEQUENCE: 78

```
gatccaagtt gtggatgcga tggtactcgg gaactactcg tcgatacgga ggtggcggc    59
```

<210> SEQ ID NO 79
<211> LENGTH: 59
<212> TYPE: DNA
<213> ORGANISM: Artificial Sequence
<220> FEATURE:
<223> OTHER INFORMATION: DNA for annealing

<400> SEQUENCE: 79

```
tcgagccgcc acctccgtat cgacgagtag ttcccgagta ccatcgcatc cacaacttg    59
```

<210> SEQ ID NO 80
<211> LENGTH: 59
<212> TYPE: DNA
<213> ORGANISM: Artificial Sequence
<220> FEATURE:
<223> OTHER INFORMATION: DNA for annealing

<400> SEQUENCE: 80

```
gatccaagtt ggctatgcga tggtactcgc caactactcg tcgatacgga ggtggcggc    59
```

<210> SEQ ID NO 81
<211> LENGTH: 59
<212> TYPE: DNA
<213> ORGANISM: Artificial Sequence
<220> FEATURE:
<223> OTHER INFORMATION: DNA for annealing

<400> SEQUENCE: 81

```
tcgagccgcc acctccgtat cgacgagtag ttggcgagta ccatcgcata gccaacttg    59
```

<210> SEQ ID NO 82
<211> LENGTH: 59
<212> TYPE: DNA
<213> ORGANISM: Artificial Sequence
<220> FEATURE:
<223> OTHER INFORMATION: DNA for annealing

<400> SEQUENCE: 82

```
gatccaggtt gtggatgcga tggtacgctc caactactcg tcgatacgga ggtggcggc    59
```

<210> SEQ ID NO 83
<211> LENGTH: 59
<212> TYPE: DNA
<213> ORGANISM: Artificial Sequence
<220> FEATURE:
<223> OTHER INFORMATION: DNA for annealing

<400> SEQUENCE: 83

```
tcgagccgcc acctccgtat cgacgagtag ttggagcgta ccatcgcatc cacaacctg    59
```

<210> SEQ ID NO 84
<211> LENGTH: 59
<212> TYPE: DNA
<213> ORGANISM: Artificial Sequence
<220> FEATURE:
<223> OTHER INFORMATION: DNA for annealing

<400> SEQUENCE: 84

```
gatccaggtt gtggatgcga tggtactcgc cagccactcg tcgatacgga ggtggcggc    59
```

<210> SEQ ID NO 85
<211> LENGTH: 59
<212> TYPE: DNA
<213> ORGANISM: Artificial Sequence
<220> FEATURE:

<223> OTHER INFORMATION: DNA for annealing

<400> SEQUENCE: 85
tcgagccgcc acctccgtat cgacgagtgg ctggcgagta ccatcgcatc cacaacctg      59

<210> SEQ ID NO 86
<211> LENGTH: 59
<212> TYPE: DNA
<213> ORGANISM: Artificial Sequence
<220> FEATURE:
<223> OTHER INFORMATION: DNA for annealing

<400> SEQUENCE: 86
gatccaggtt gtggatgcga tggtactcgc caactgctcg tcgatacgga ggtggcggc      59

<210> SEQ ID NO 87
<211> LENGTH: 59
<212> TYPE: DNA
<213> ORGANISM: Artificial Sequence
<220> FEATURE:
<223> OTHER INFORMATION: DNA for annealing

<400> SEQUENCE: 87
tcgagccgcc acctccgtat cgacgagcag ttggcgagta ccatcgcatc cacaacctg      59

<210> SEQ ID NO 88
<211> LENGTH: 59
<212> TYPE: DNA
<213> ORGANISM: Artificial Sequence
<220> FEATURE:
<223> OTHER INFORMATION: DNA for annealing

<400> SEQUENCE: 88
gatccaggtt gattatgcga atctactcgc caactactcg tcgatacgga ggtggcggc      59

<210> SEQ ID NO 89
<211> LENGTH: 59
<212> TYPE: DNA
<213> ORGANISM: Artificial Sequence
<220> FEATURE:
<223> OTHER INFORMATION: DNA for annealing

<400> SEQUENCE: 89
tcgagccgcc acctccgtat cgacgagtag ttggcgagta gattcgcata atcaacctg      59

<210> SEQ ID NO 90
<211> LENGTH: 59
<212> TYPE: DNA
<213> ORGANISM: Artificial Sequence
<220> FEATURE:
<223> OTHER INFORMATION: DNA for annealing

<400> SEQUENCE: 90
gatccaggtt gtggatgcga tggtacgctc cagctgctcg tcgatacgga ggtggcggc      59

<210> SEQ ID NO 91
<211> LENGTH: 59
<212> TYPE: DNA
<213> ORGANISM: Artificial Sequence
<220> FEATURE:
<223> OTHER INFORMATION: DNA for annealing

<400> SEQUENCE: 91
tcgagccgcc acctccgtat cgacgagcag ctggagcgta ccatcgcatc cacaacctg      59

<210> SEQ ID NO 92

-continued

<210> SEQ ID NO 92
<211> LENGTH: 59
<212> TYPE: DNA
<213> ORGANISM: Artificial Sequence
<220> FEATURE:
<223> OTHER INFORMATION: DNA for annealing

<400> SEQUENCE: 92
gatccaggtt gatcatgcga atctacgctc caactactcg tcgatacgga ggtggcggc    59

<210> SEQ ID NO 93
<211> LENGTH: 59
<212> TYPE: DNA
<213> ORGANISM: Artificial Sequence
<220> FEATURE:
<223> OTHER INFORMATION: DNA for annealing

<400> SEQUENCE: 93
tcgagccgcc acctccgtat cgacgagtag ttggagcgta gattcgcatg atcaacctg    59

<210> SEQ ID NO 94
<211> LENGTH: 59
<212> TYPE: DNA
<213> ORGANISM: Artificial Sequence
<220> FEATURE:
<223> OTHER INFORMATION: DNA for annealing

<400> SEQUENCE: 94
gatccaggtt gtatatgcga tattactcgc caactactcg tcgatacgga ggtggcggc    59

<210> SEQ ID NO 95
<211> LENGTH: 59
<212> TYPE: DNA
<213> ORGANISM: Artificial Sequence
<220> FEATURE:
<223> OTHER INFORMATION: DNA for annealing

<400> SEQUENCE: 95
tcgagccgcc acctccgtat cgacgagtag ttggcgagta atatcgcata tacaacctg    59

<210> SEQ ID NO 96
<211> LENGTH: 59
<212> TYPE: DNA
<213> ORGANISM: Artificial Sequence
<220> FEATURE:
<223> OTHER INFORMATION: DNA for annealing

<400> SEQUENCE: 96
gatccaggtt gtggatgcga tggtactcgc cacggactcg tgcctacgga ggtggcggc    59

<210> SEQ ID NO 97
<211> LENGTH: 59
<212> TYPE: DNA
<213> ORGANISM: Artificial Sequence
<220> FEATURE:
<223> OTHER INFORMATION: DNA for annealing

<400> SEQUENCE: 97
tcgagccgcc acctccgtag gcacgagtcc gtggcgagta ccatcgcatc cacaacctg    59

<210> SEQ ID NO 98
<211> LENGTH: 59
<212> TYPE: DNA
<213> ORGANISM: Artificial Sequence
<220> FEATURE:
<223> OTHER INFORMATION: DNA for annealing

<400> SEQUENCE: 98
gatccggata ccgacgcacg accccgtcct actggagaat gtggctcagg ggtggcggc    59

<210> SEQ ID NO 99
<211> LENGTH: 59
<212> TYPE: DNA
<213> ORGANISM: Artificial Sequence
<220> FEATURE:
<223> OTHER INFORMATION: DNA for annealing

<400> SEQUENCE: 99
tcgagccgcc acccctgagc cacattctcc agtaggacgg ggtcgtgcgt cggtatccg    59

<210> SEQ ID NO 100
<211> LENGTH: 59
<212> TYPE: DNA
<213> ORGANISM: Artificial Sequence
<220> FEATURE:
<223> OTHER INFORMATION: DNA for annealing

<400> SEQUENCE: 100
gatccattcc gtcgcgctgg aaggaccaat tctggaagcg gtggcactac ggtggcggc    59

<210> SEQ ID NO 101
<211> LENGTH: 59
<212> TYPE: DNA
<213> ORGANISM: Artificial Sequence
<220> FEATURE:
<223> OTHER INFORMATION: DNA for annealing

<400> SEQUENCE: 101
tcgagccgcc accgtagtgc caccgcttcc agaattggtc cttccagcgc gacggaatg    59

<210> SEQ ID NO 102
<211> LENGTH: 59
<212> TYPE: DNA
<213> ORGANISM: Artificial Sequence
<220> FEATURE:
<223> OTHER INFORMATION: DNA for annealing

<400> SEQUENCE: 102
gatccaagaa cgcatggaaa cattcgagct gccatcaccg tcatcaaatc ggtggcggc    59

<210> SEQ ID NO 103
<211> LENGTH: 59
<212> TYPE: DNA
<213> ORGANISM: Artificial Sequence
<220> FEATURE:
<223> OTHER INFORMATION: DNA for annealing

<400> SEQUENCE: 103
tcgagccgcc accgatttga tgacggtgat ggcagctcga atgtttccat gcgttcttg    59

<210> SEQ ID NO 104
<211> LENGTH: 59
<212> TYPE: DNA
<213> ORGANISM: Artificial Sequence
<220> FEATURE:
<223> OTHER INFORMATION: DNA for annealing

<400> SEQUENCE: 104
gatccctcat cacgaagcag tacagatacc cgtccagacg acggtttaac ggtggcggc    59

<210> SEQ ID NO 105
<211> LENGTH: 59
<212> TYPE: DNA
<213> ORGANISM: Artificial Sequence
<220> FEATURE:

```
<223> OTHER INFORMATION: DNA for annealing

<400> SEQUENCE: 105
tcgagccgcc accgttaaac cgtcgtctgg acgggtatct gtactgcttc gtgatgagg      59

<210> SEQ ID NO 106
<211> LENGTH: 59
<212> TYPE: DNA
<213> ORGANISM: Artificial Sequence
<220> FEATURE:
<223> OTHER INFORMATION: DNA for annealing

<400> SEQUENCE: 106
gatcccagca acatctgctc atcgcaatca acggataccc acgatacaat ggtggcggc      59

<210> SEQ ID NO 107
<211> LENGTH: 59
<212> TYPE: DNA
<213> ORGANISM: Artificial Sequence
<220> FEATURE:
<223> OTHER INFORMATION: DNA for annealing

<400> SEQUENCE: 107
tcgagccgcc accattgtat cgtgggtatc cgttgattgc gatgagcaga tgttgctgg      59

<210> SEQ ID NO 108
<211> LENGTH: 59
<212> TYPE: DNA
<213> ORGANISM: Artificial Sequence
<220> FEATURE:
<223> OTHER INFORMATION: DNA for annealing

<400> SEQUENCE: 108
gatccaagcg accaacgatg cgattccgat acacatggaa tcctatgaag ggtggcggc      59

<210> SEQ ID NO 109
<211> LENGTH: 59
<212> TYPE: DNA
<213> ORGANISM: Artificial Sequence
<220> FEATURE:
<223> OTHER INFORMATION: DNA for annealing

<400> SEQUENCE: 109
tcgagccgcc acccttcata ggattccatg tgtatcggaa tcgcatcgtt ggtcgcttg      59

<210> SEQ ID NO 110
<211> LENGTH: 59
<212> TYPE: DNA
<213> ORGANISM: Artificial Sequence
<220> FEATURE:
<223> OTHER INFORMATION: DNA for annealing

<400> SEQUENCE: 110
gatcctggaa gtgccgtcgc caatgcttcc gtgtactgca tcattggaat ggtggcggc      59

<210> SEQ ID NO 111
<211> LENGTH: 59
<212> TYPE: DNA
<213> ORGANISM: Artificial Sequence
<220> FEATURE:
<223> OTHER INFORMATION: DNA for annealing

<400> SEQUENCE: 111
tcgagccgcc accattccaa tgatgcagta cacggaagca ttggcgacgg cacttccag      59

<210> SEQ ID NO 112
```

```
<211> LENGTH: 59
<212> TYPE: DNA
<213> ORGANISM: Artificial Sequence
<220> FEATURE:
<223> OTHER INFORMATION: DNA for annealing

<400> SEQUENCE: 112
gatcctggaa ggcgcgtcgc caatgcttcc gtgtactgca tcattggaat ggtggcggc      59

<210> SEQ ID NO 113
<211> LENGTH: 59
<212> TYPE: DNA
<213> ORGANISM: Artificial Sequence
<220> FEATURE:
<223> OTHER INFORMATION: DNA for annealing

<400> SEQUENCE: 113
tcgagccgcc accattccaa tgatgcagta cacggaagca ttggcgacgc gccttccag      59

<210> SEQ ID NO 114
<211> LENGTH: 59
<212> TYPE: DNA
<213> ORGANISM: Artificial Sequence
<220> FEATURE:
<223> OTHER INFORMATION: DNA for annealing

<400> SEQUENCE: 114
gatcctggaa gtgccgtcgc caagctttcc gtgtactgca tcattggaat ggtggcggc      59

<210> SEQ ID NO 115
<211> LENGTH: 59
<212> TYPE: DNA
<213> ORGANISM: Artificial Sequence
<220> FEATURE:
<223> OTHER INFORMATION: DNA for annealing

<400> SEQUENCE: 115
tcgagccgcc accattccaa tgatgcagta cacggaaagc ttggcgacgg cacttccag      59

<210> SEQ ID NO 116
<211> LENGTH: 70
<212> TYPE: DNA
<213> ORGANISM: Artificial Sequence
<220> FEATURE:
<223> OTHER INFORMATION: primer

<400> SEQUENCE: 116
catgccatgg atgggagggt cccatcacca ccatcatcac ggaggtatgg tgagcaaggg      60
cgaggagctg                                                            70

<210> SEQ ID NO 117
<211> LENGTH: 29
<212> TYPE: DNA
<213> ORGANISM: Artificial Sequence
<220> FEATURE:
<223> OTHER INFORMATION: primer

<400> SEQUENCE: 117
gcggatcccg gccgctttac ttgtacagc                                       29

<210> SEQ ID NO 118
<211> LENGTH: 75
<212> TYPE: DNA
<213> ORGANISM: Artificial Sequence
<220> FEATURE:
<223> OTHER INFORMATION: primer
```

-continued

```
<400> SEQUENCE: 118
tggatgcgtt ggtacagccc tactacgcgt aggtacggag gacatatggg catggtgagc    60
aagggcgagg agctg                                                    75

<210> SEQ ID NO 119
<211> LENGTH: 78
<212> TYPE: DNA
<213> ORGANISM: Artificial Sequence
<220> FEATURE:
<223> OTHER INFORMATION: primer

<400> SEQUENCE: 119
gccatgggag ggtcccatca ccaccatcat cacggtaccg gaaagttgtg gatgcgttgg    60
tacagcccta ctacgcgt                                                 78

<210> SEQ ID NO 120
<211> LENGTH: 4
<212> TYPE: PRT
<213> ORGANISM: Artificial Sequence
<220> FEATURE:
<223> OTHER INFORMATION: linker

<400> SEQUENCE: 120

Gly Gly Gly Ser
1

<210> SEQ ID NO 121
<211> LENGTH: 5
<212> TYPE: PRT
<213> ORGANISM: Artificial Sequence
<220> FEATURE:
<223> OTHER INFORMATION: linker

<400> SEQUENCE: 121

Gly Gly Gly Ser Ser
1               5
```

CELL PENETRATING PEPTIDE

TECHNICAL FIELD

The present invention relates to a novel cell penetrating peptide and a pharmaceutical containing the peptide.

BACKGROUND TECHNOLOGY

While general proteins, nucleic acids in therapeutic or diagnostic use do not penetrate the cell membrane, it has recently been found that there are peptides that transport proteins, nucleic acids into cells and nuclei in living organisms (hereinafter also referred to as "TAT proteins") (non-patent document 1 to non-patent document 3). Furthermore, it has been found that a fusion protein of a peptide consisting of 11 particular amino acids of the TAT proteins with another protein penetrates the cell membrane; such regions essential for cell membrane passage, i.e., cell penetrating peptides, are called PTDs (Protein Transduction Domains) (non-patent document 4).

To date, methods have been developed for transporting proteins, nucleic acids into cells by means of various cell penetrating peptides. Specifically, a method utilizing a particular partial polypeptide of the HIV-1 TAT protein (patent document 1) has been proposed.

However, cell penetrating peptides that have conventionally been used exist naturally, posing the problem of low translocation efficiency. For this reason, there has been a demand for the development of a peptide having a high transportation efficiency.

Patent document 1: JP-A-HEI-10-33186
Non-patent document 1: Green, M. et al. Cell 55, 1179-1188 (1988)
Non-patent document 2: Frankel, A. D. et al. Cell 55, 1189-1193 (1988)
Non-patent document 3: Fawell, S. et al. Proc. Natl. Acad. Sci. 91, 664-668 (1994)
Non-patent document 4: Nagahra, H. et al. Nature Medicine 4, 1449-1452 (1998)

DISCLOSURE OF THE INVENTION

Problems to Be Solved by the Invention

It is an object of the present invention to provide a novel cell penetrating peptide and a pharmaceutical containing the peptide.

Means for Solving the Problems

The present inventors diligently investigated to provide a peptide consisting of a novel amino acid sequence, useful as a cell penetrating peptide, identified the amino acid sequence of a peptide that transports proteins into cells at higher frequency than conventional cell penetrating peptides, and developed the present invention. Specifically, the present inventors discovered a peptide with high intracellular transferability, in a random peptide library of $10^{12}$ molecules by comprehensive screening. Peptides selected using this technique are thought to be particularly highly transferable among the peptides with the capability of intracellular translocation.

Accordingly, the present invention is as follows:
(1) A peptide having the amino acid sequence shown below.
B-X-Z-X-Arg-Z-Tyr-J-X-$O^1$-X-Arg-$O^2$-X-X or X-X-$O^1$-Arg-X-$O^2$-X-J-Tyr-Z-Arg-X-Z-X-B
wherein (i) B is arginine or lysine, (ii) at least one of $O^1$ or $O^2$ is arginine, (iii) Z is a hydrophobic amino acid, (iv) J is serine or alanine, and (v) X is an arbitrarily chosen amino acid.
(2) The peptide according to (1), consisting of the amino acid sequence shown by any one of SEQ ID NOS:1 to 34 in the sequence listing wherein one or a plurality of amino acids have been substituted, deleted, added or inserted.
(3) A peptide consisting of the amino acid sequence shown by any one of SEQ ID NOS:35 to 47 in the sequence listing wherein one or a plurality of amino acids have been substituted, deleted, added or inserted, and the reversed-chain peptide thereof.
(4) A peptide consisting of the amino acid sequence shown by any one of SEQ ID NOS:1 to 47 in the sequence listing, and the reversed-chain peptide thereof.
(5) A DNA consisting of the DNA sequence that encodes the peptide according to any one of (1) to (4) above.
(6) A recombinant vector containing the DNA according to (5) above.
(7) A transformant comprising the recombinant vector according to (6) above.
(8) A peptide-bound substance containing the peptide according to any one of (1) to (4) above and a bioactive substance.
(9) The peptide-bound substance according to (8) above, wherein the bioactive substance is a protein having a bioactivity, a polypeptide having a bioactivity, a drug-encapsulated liposome, a polyethylene-glycolated drug-encapsulated liposome, a low-molecular compound, a nucleic acid, a magnetic bead, a nano-gauge particle or a phage.
(10) The peptide-bound substance according to (8) above, wherein the protein having a bioactivity is an about 10 KDa to about 120 KDa protein or a peptide having 4 to 30 amino acids.
(11) The peptide-bound substance according to (8) above, wherein the protein having a bioactivity is mi-transcription factor (MITF).
(12) The peptide-bound substance according to any one of (8) to (11) above, which is transported into cells and/or into nuclei.
(13) The peptide-bound substance according to any one of (8) to (11) above, which is transported into cells.
(14) A pharmaceutical containing the peptide-bound substance according to (8) above.
(15) The pharmaceutical according to (14) above, which is used as an anti-allergic drug.

Effect of the Invention

According to the present invention, it is possible to provide a cell penetrating peptide that transports proteins into cells and/or into nuclei at a higher frequency than conventional cell penetrating peptides, and a pharmaceutical containing the peptide.

BEST MODE FOR CARRYING OUT THE INVENTION

Figure 1:
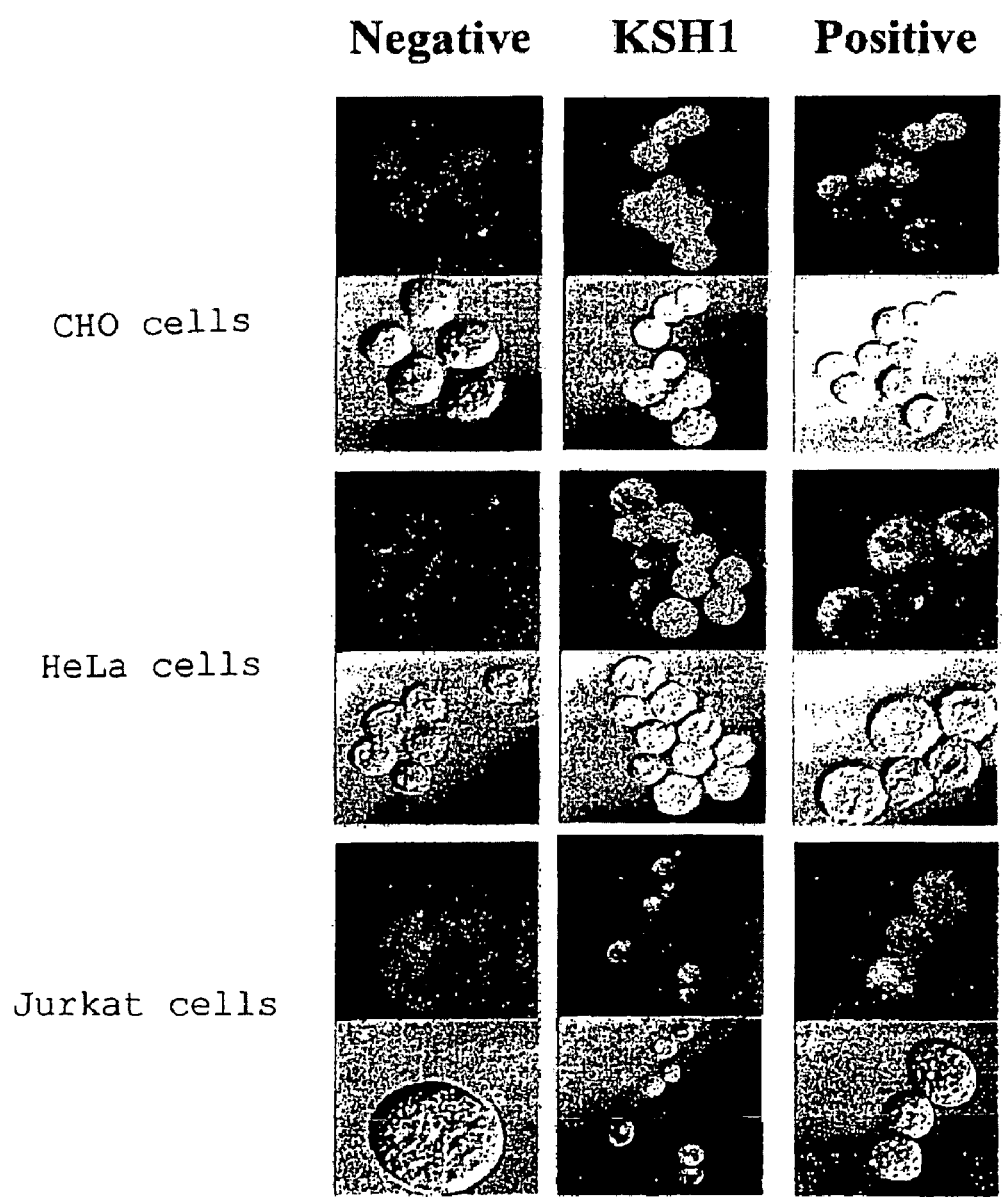
FIG. 1 A representation showing results of an intracellular translocation test of a fluorescence-labeled peptide. The upper panels show fluorescence from FITC; the lower panels show differential interference microscopic images of cells in combination with fluorescence images.

The present invention is hereinafter described in detail.

(1) Peptides

In the present invention, peptides include the L-form or D-form of a peptide having the amino acid sequence B-X-Z-X-Arg-Z-Tyr-J-X-O$^1$-X-Arg-O$^2$-X-X or X-X-O$^1$-Arg-X-O$^2$-X-J-Tyr-Z-Arg-X-Z-X-B. In this amino acid sequence, B is arginine or lysine, and at least one of O$^1$ or O$^2$ is arginine, and Z is a hydrophobic amino acid, and J is serine or alanine, and X is an arbitrarily chosen amino acid. Here, B is desirably arginine. If at least one of O$^1$ or O$^2$ is arginine, the other may be an arbitrarily chosen amino acid. The hydrophobic amino acid for Z is any one of leucine, phenylalanine, isoleucine, valine, tyrosine, and tryptophan, and is desirably leucine, phenylalanine, isoleucine or tryptophan, and is most desirably isoleucine or tryptophan.

Having the amino acid sequence B-X-Z-X-Arg-Z-Tyr-J-X-O$^1$-X-Arg-O$^2$-X-X or X-X-O$^1$-Arg-X-O$^2$-X-J-Tyr-Z-Arg-X-Z-X-B may be having an amino acid sequence of the 15 amino acids shown by the above-described sequences only, or may be having one or a plurality of arbitrarily chosen amino acids on the C-terminal side and/or N-terminal side of the above-described amino acid sequence. Also meant by the same is that the peptide is capable of transporting proteins into cells and/or into nuclei. The arbitrarily chosen amino acids are not particularly limited, and are desirably basic amino acids (arginine, histidine, lysine), tryptophan, proline, glycine, cysteine and alanine, more desirably glycine, cysteine and arginine. The number thereof is not particularly limited.

As a more desirable peptide of the peptides shown by the amino acid sequence B-X-Z-X-Arg-Z-Tyr-J-X-O$^1$-X-Arg-O$^2$-X-X or X-X-O$^1$-Arg-X-O$^2$-X-J-Tyr-Z-Arg-X-Z-X-B, the L-form or D-form of a peptide consisting of one of the amino acid sequences shown by SEQ ID NOS:1 to 34 in the sequence listing and the reversed-chain peptide thereof can be mentioned. As a still more desirable peptide, the L-form or D-form of a peptide consisting of the amino acid sequence shown by SEQ ID NO:1, 2, 4, 7, 8, 9, 10, 11, 13, 17, 18, 19, 20, 22, 24, 25, 26, 27, 28, 29, 30, 32, 33 or 34 in the sequence listing can be mentioned. The most desirable peptide is the amino acid shown by SEQ ID NO:1, 7, 8, 9, 11, 13, 17, 18, 19, 20, 22, 25, 26, 27, 29, 30, 32, 33 or 34 in the sequence listing.

In the present invention, a reversed-chain peptide refers to a peptide obtained by reverting the arrangement of amino acids from the N-terminus to C-terminus of a certain sequence, for example, (N-terminus)-A-B-C-D-(C-terminus), to have the peptide (N-terminus)-D-C-B-A-(C-terminus).

In the present invention, peptides also include, in addition to the aforementioned peptides, peptides having the L-form or D-form of a peptide shown by one of SEQ ID NOS:35 to 47 in the sequence listing and the reversed-chain peptide thereof. Particularly desirable of these peptides are the L-form or D-form of a peptide consisting of the amino acid sequence shown by SEQ ID NO:35, 36, 38, 39, 42, 43, 45, 46 or 47 in the sequence listing.

Having the L-form or D-form of a peptide and the reversed-chain peptide thereof means arbitrary having one or a plurality of amino acids on the C-terminal side and/or N-terminal side of the 15 amino acid sequences shown by one of SEQ ID NOS:35 to 47 in the sequence listing. Also meant by the same is that the peptide is capable of transporting proteins into cells and/or into nuclei. Although the arbitrarily chosen amino acids are not particularly limited, basic amino acids (arginine, histidine, lysine), tryptophan, proline, glycine, cysteine and alanine are desirable, and glycine, cysteine and arginine are more desirable. The number thereof is not particularly limited.

Furthermore, the peptides of the present invention shown by SEQ ID NOS:1 to 47 in the sequence listing include peptides having an amino acid sequence wherein 1 or 2 or more amino acids have been deleted, added, inserted or substituted by other amino acids, or peptides having an amino acid sequence consisting of a combination thereof. Also meant by the same is that the peptide has the capability of translocation to cells. In this case, even if an amino acid has been inserted, deleted or substituted, amino acid sequences capable of transporting proteins into cells and/or into nuclei at a frequency similar to that for the peptides shown by SEQ ID NOS:1 to 47 in the sequence listing can be mentioned. If an amino acid has been inserted, deleted or substituted, the position of the insertion, deletion or substitution is not particularly limited.

The present invention particularly includes a peptide having three C-terminal amino acids deleted from the peptide shown by the sequence B-X-Z-X-Arg-Z-Tyr-J-X-$O^1$-X-Arg-$O^2$-X-X. The peptide may be a peptide having 1 or 2 C-terminal amino acids deleted.

Here, the peptides consisting of the amino acid sequences shown by SEQ ID NOS:1 to 47 in the sequence listing are novel sequences without homology to any known PTDs that have been reported to date, and exhibited no homology to any human cDNA sequences that have been reported to date.

A peptide of the present invention can be prepared according to a commonly known method of peptide synthesis, and substitution, addition or deletion can easily be achieved by changing the kind of protected amino acid. Special amino acids such as D-amino acid and sarcosine (N-methylglycine) may be introduced. Methods of peptide synthesis include, for example, solid phase synthesis, liquid phase synthesis; after the synthetic reaction, a peptide used in the present invention can be purified and isolated by combining ordinary methods of purification, for example, solvent extraction, distillation, column chromatography, liquid chromatography or recrystallization.

Commonly known methods of peptide synthesis include, for example, methods described in (i) to (v) below.
(i) M. Bodanszky and M. A. Ondetti, Peptide Synthesis, Interscience Publishers, New York, (1966)
(ii) Schroeder and Luebke, The Peptide, Academic Press, New York, 1965
(iii) Nobuo Izumiya, et al.: Peptide Gosei-no-Kiso to Jikken, published by Maruzen Co. (1975)
(iv) Haruaki Yajima and Shunpei Sakakibara: Seikagaku Jikken Koza 1, Tanpakushitsu no Kagaku IV, 205 (1977)
(v) Haruaki Yajima, ed.: Zoku Iyakuhin no Kaihatsu, Vol. 14, Peptide Synthesis, Hirokawa Shoten (2) DNA Sequences and DNAs In the present invention, DNAs include a DNA consisting of the DNA sequence that encodes the peptide represented by the amino acid sequence shown by one of SEQ ID NOS:1 to 47 in the sequence listing; specifically, such DNAs include, but are not limited to, a DNA consisting of the DNA sequence shown by SEQ ID NO:48 or 49 in the sequence listing. The DNA sequence shown by SEQ ID NO:48 or 49 in the sequence listing encodes the amino acid sequence shown by SEQ ID NO:33 or 34 in the sequence listing, respectively.

In the present invention, the DNA contains a DNA consisting of a DNA sequence that hybridizes with a complementary strand of the DNA consisting of the DNA sequence that encodes the peptide shown by one of SEQ ID NOS:1 to 47 in the sequence listing under stringent conditions.

In the present invention, the DNA sequence that hybridizes under stringent conditions contains a DNA sequence having a homology of about 80% or more, preferably about 90% or more, more preferably about 95% or more, to a complementary strand of the DNA sequence that encodes the peptide shown by SEQ ID NO:1 or 2 in the sequence listing. Hybridization can be performed according to a commonly known method or a method based thereon, for example, a method described in Molecular Cloning, 2nd edition (J. Sambrook et al., Cold Spring Harbor Lab. Press, 1989) and the like. High-stringent conditions refer to, for example, conditions involving a sodium concentration of about 19 mM to about 40 mM, preferably about 19 mM to about 20 mM, and a temperature of about 50° C. to about 70° C., preferably about 60° C. to about 65° C. In particular, a case wherein the sodium concentration is about 19 mM and the temperature is about 65° C. is the most preferable.

The DNA sequences of the present invention include sequences having an identity of about 50% or more to the DNA sequences that encode the peptides shown by SEQ ID NOS:1 to 47 in the sequence listing. The DNA sequences of the present invention contain a DNA sequence having an identity of preferably about 60% or more, more preferably about 70% or more, still more preferably about 80% or more, still yet more preferably about 90% or more, even more preferably about 95% or more.

The DNA sequences of the present invention include the DNA sequences that encode the peptides shown by SEQ ID NOS:1 to 47 in the sequence listing wherein bases have been inserted, deleted or substituted. Here, as the number of bases inserted, deleted or substituted, 1 base or 2 bases or more can be mentioned; for example, 1 base to 10 bases, preferably 1 base to 5 bases, can be mentioned. In this case, even if a base has been inserted, deleted or substituted, a DNA sequence capable of transporting proteins into cells and/or into nuclei at a frequency similar to that for the DNA sequences that encode the peptides shown by SEQ ID NOS:1 to 47 in the sequence listing can be mentioned. If a base has been inserted, deleted or substituted, the position of the insertion, deletion or substitution is not particularly limited.

A DNA of the present invention can be synthesized according to a commonly known method. A cDNA that encodes a fusion protein, if prepared, can be obtained by amplification by a PCR method using primers.

Primers that can be used in the present invention include, for example, a primer for use in preparing a cDNA that encodes a fusion protein with a green fluorescent protein eGFP (Enhanced Green Fluorescent Protein).

(3) Recombinant Vectors and Transformants

Recombinant vectors used in the present invention include vectors that can be expressed in prokaryotic cells such as of *Escherichia coli* (for example, pBR322, pUC119 or derivatives thereof). Furthermore, in eukaryotic cells, expression vectors for yeast include, for example, plasmid vectors such as pAUR112 (Takara Bio Inc.). Vectors that can be expressed in cells derived from mammals include, for example, plasmid vectors like pcDNA3.1 (Invitrogen) and viral vectors such as pDON-AI DNA (Takara Bio Inc.).

A recombinant vector of the present invention are prepared by recombining the entire or a portion of a DNA having the DNA sequence of the present invention with these recombinant vectors by a commonly known method.

A recombinant vector can be obtained by, for example, a method described in Molecular Cloning, 2nd (J. Sambrook et al., Cold Spring Harbor Lab. Press, 1989).

A transformant of the present invention refers to a transformant comprising a recombinant vector of the present invention. As the host, *Escherichia coli*, yeast, animal cells and the like can be used. *Escherichia coli* is preferable. Auxotrophs and antibiotic-sensitive strains can also be used as hosts.

A transformant of the present invention can be prepared according to a commonly known method. For example, transformation can be performed according to methods described in Molecular Cloning, 2nd (J. Sambrook et al., Cold Spring Harbor Lab. Press, 1989), such as the protoplast polyethylene glycol method and electroporation method.

(4) Peptide-Bound Substances

In the present invention, peptide-bound substances include one containing the peptide shown by the amino acid sequence: B-X-Z-X-Arg-Z-Tyr-J-X-$O^1$-X-Arg-$O^2$-X-X or X-X-$O^1$-Arg-X-$O^2$-X-J-Tyr-Z-Arg-X-Z-X-B or the peptide consisting of the amino acid sequence shown by one of SEQ ID NOS:1 to 47 in the sequence listing and a bioactive substance.

In the present invention, the peptide shown by the amino acid sequence: B-X-Z-X-Arg-Z-Tyr-J-X-$O^1$-X-Arg-$O^2$-X-X or X-X-$O^1$-Arg-X-$O^2$-X-J-Tyr-Z-Arg-X-Z-X-B or the peptide shown by one of SEQ ID NOS:1 to 47 in the sequence listing can be utilized as a cell penetrating peptide; by binding a peptide of the present invention to a bioactive substance, the bioactive substance can be transported into cells and/or into nuclei. More preferably, a bioactive substance is transported into cells. Here, the cells are animal cells, particularly human cells. The human cells may be adhesive cells or floating cells, and may be cells that configure various organs in living organisms.

In the present invention, bioactive substances include proteins having a bioactivity, peptides having a bioactivity, drug-encapsulated liposomes, polyethylene-glycolated drug-encapsulated liposomes (hereinafter also referred to as "PEGylated drug-encapsulated liposomes"), low-molecular compounds, nucleic acids, magnetic beads, nano-gauge particles and phages.

Here, proteins having a bioactivity include proteins for the treatment, prevention and/or diagnosis of disease and the like, being about 10 KDa to about 500 KDa proteins; about 10 KDa to about 120 KDa proteins are particularly desirable. Specifically, such proteins include, but are not limited to, enzymes, antibodies, transcription factors and partial peptides thereof. Enzymes include SOD (Molecules and Cells 2005, 19, 191-197, W. S. Eum et al.). Antibodies include antibodies against intracellular proteins, single-chain antibody, antibodies against foreign proteins such as viruses and the like (Current Molecular Medicine 2004, 4, 519-528, M. N. Lobato and T. H. Rabbitts, Molecular Therapy 2003, 8, 355-366, Y. Y. Wheeler et al. and the like). Transcription factors include mi-transcription factor (microphthalmia-associated transcription factor: hereinafter also referred to as "MITF") and the like. Here, MITF is a kind of transcription regulatory factor existing in living organisms, being a protein capable of regulating c-kit gene expression, characteristic of mast cells. Specifically, such transcription factors include, but are not limited to, the various MITFs described in JP-A-2004-201547.

In the present invention, polypeptides having a bioactivity include peptides for the treatment, prevention and/or diagnosis of disease and the like, being peptides having 2 to 100 amino acids; peptides having 4 to 30 amino acids are particularly desirable. Specifically, such peptides include, but are not limited to, HSP (Heat Shock Protein) 20 analogue peptide (J Appl Physiol 98: 1836-1845, 2005), the KLAK antibacterial peptide (Cancer Research 61, 7709-7712, 2001), HIF-1α (Proc Natl Acad Sci USA 99: 10423-10428, 2002), PKC (Protein Kinase C) δ inhibitory peptide (Proc Natl Acad Sci USA 98: 11114-11119, 2001), VIVIT (Nature Medicine 10: 305-309, 2004) and the like.

In the present invention, liposomes include small unilamellar vesicles (hereinafter also referred to as "SUV"), large unilamellar vesicles (hereinafter also referred to as "LUV"), multilamellar vesicles (hereinafter also referred to as "MLV") and the like; SUV or LUV is preferable. Furthermore, drug-encapsulated liposomes include anti-inflammatory drugs such as diclofenac sodium and tobramycin encapsulated in liposomes described above.

In the present invention, PEGylated drug-encapsulated liposomes include a drug-encapsulated liposome having polyethylene glycol (PEG) bound to the surface thereof.

A drug-encapsulated liposome or PEGylated drug-encapsulated liposome in the present invention can be prepared by methods described in JP-A-HEI-4-346918, JP-A-HEI-10-29930, the pamphlet for International Patent Application Publication No. 97/29128 or the pamphlet for International Patent Application Publication No. 01/064743.

In the present invention, low-molecular compounds include, for example, anti-inflammatory drugs such as diclofenac sodium, tobramycin and cyclosporine.

In the present invention, nucleic acids include, for example, plasmids, siRNAs and antisense DNA for disease-related genes.

In the present invention, magnetic beads include, for example, supermagnetic ion oxide particles introduced to T cells, B cells, or macrophage for tracking the localization of such cells by MRI (Advanced Drug Delivery Reviews 57: 637-651, 2005).

In the present invention, nano-gauge particles include, for example, nano-sized particles having proteins, low-molecular compounds, nucleic acids, polysaccharides and the like encapsulated therein (Advanced Drug Delivery Reviews 57: 637-651, 2005).

In the present invention, phages include, for example, M13 phages incorporating various cDNA expression units (Advanced Drug Delivery Reviews 57: 529-546, 2005).

In the present invention, a peptide-bound substance containing a peptide of the present invention and a protein having a bioactivity as described above can be obtained by culturing host cells transformed using a recombinant vector comprising a DNA that encodes the substance, and isolating the protein produced thereby by a method such as high performance liquid chromatography (HPLC). The DNA used here may be a DNA comprising a fusion of the gene that encodes the peptide of the present invention and the gene that encodes a protein or polypeptide having a bioactivity as described above. Alternatively, to obtain a peptide-bound substance containing a peptide of the present invention and a protein having a bioactivity, the respective genes may be expressed to acquire the peptide of the present invention and the protein or polypeptide having a bioactivity, and they may be fused by a chemical reaction. As a means of the fusion by a chemical reaction, disulfide linkage using a cysteine residue and the like can be mentioned. Alternatively, a peptide-bound substance containing a peptide of the present invention and a protein having a bioactivity can be prepared by a method using a chemical crosslinking agent. In this case, it is preferable to prevent crosslinking between the peptide of the present invention and the functional active site of the protein having a bioactivity; as the method of chemical crosslinking, a method described in JP-A-HEI-10-33186 and the like can be mentioned.

Furthermore, by using a method of chemical crosslinking, a peptide of the present invention can also be bound to a drug-encapsulated liposome, a PEGylated drug-encapsulated liposome or a low-molecular compound.

By binding a peptide in the present invention to a drug-encapsulated liposome or a PEGylated drug-encapsulated liposome, the drug encapsulated in the liposome can be delivered into cells. Methods of peptide binding in the present invention include, for example, a method wherein a cysteine residue is introduced to the N-terminus or C-terminus, and binding the peptide to a drug-encapsulated liposome having a maleimide group or a PEGylated drug-encapsulated liposome via an SH group and the like.

(5) Pharmaceuticals

A peptide-bound substance of the present invention can be utilized as a pharmaceutical. Furthermore, a desired bioactive substance can be transported into cells and/or into nuclei by binding a peptide in the present invention to the bioactive substance; therefore, depending on the kind of the bioactive substance to be bound, the peptide of the present invention can be utilized as a therapeutic drug and/or prophylactic drug for a wide variety of diseases. The bioactive substance to be bound to the peptide of the present invention is preferably a protein having a bioactivity. More preferably, by binding a peptide of the present invention to an MITF mutant, the peptide of the present invention can be utilized as an antiallergic drug.

If used as a pharmaceutical, a peptide-bound substance in the present invention can be prepared as a preparation and administered according to a commonly known method. For example, the peptide-bound substance can be administered to humans or other mammals in the form of a liquid as is, or as a pharmaceutical composition in the form an appropriate dosage form, orally or parenterally.

For producing a solution and the like, an appropriate solvent or suspending agent can be used.

In producing tablets or capsules as an appropriate dosage form, an appropriate excipient can be used. Liquid preparations for oral administration, i.e., syrups, suspensions, solutions and the like, comprise a commonly used inert diluent. The preparations can also comprise, in addition to the inert diluent, auxiliaries, for example, wetting agents, suspension aids, sweetening agents, flavoring agents, coloring agents, preservatives, stabilizers and the like.

The dosage of a peptide-bound substance in the present invention for humans is determined according to the age, body weight, general health status, sex, diets, duration of administration, method of administration, excretion rate, combination of drugs, and the severity of the patient's condition being treated, in consideration of these and other factors. For example, the dosage is about 0.01 mg/Kg to about 1.0 mg/Kg, and can be administered once daily or in divided portions.

EXAMPLES

The present invention is hereinafter described specifically on the basis of the following examples, to which, however, the present invention is never limited.

Example 1

Cell Membrane Passage Test Using Synthetic Peptides

Example 1-1

Section of Cell Penetrating Peptide Sequences

Intracellularly transferable peptide sequences were concentrated according to a method described in JP-A-2005-13073, using a library of Jurkat cells (ATCC NO. TIB-152). Specifically, after a library of in vitro viruses presenting random peptides of 15 amino acids (hereinafter abbreviated IVVs) (library scale 1012) was prepared, the library was added to HeLa cells (ATCC NO. CCL2) or Jurkat cells. After cDNAs of IVVs that had translocated into the cells were recovered by PCR, IVVs were again prepared and added to the cells. By repeating the addition-recovery operation, "the peptides that translocation into cells" being present in the library were concentrated. To identify the libraries wherein the intracellularly transferable peptides had been concentrated in the various concentration operation stages, 11 kinds of amino acid sequences were arbitrary selected from the libraries after the 5th to 8th concentration operations, and the peptides were examined for the capability of intracellular translocation.

Example 1-2

Confocal Microscopic Analysis

With the PTD derived from HIV TAT protein shown by SEQ ID NO:50 in the sequence listing as the positive control (in FIG. 1 to FIG. 3, denoted by "Positive" or "TAT"), and a mutant of the TAT-derived PTD shown by SEQ ID NO:51 in the sequence listing, reported by Ulo Langel et al. (Cell-Penetrating Peptides: Processes and Applications, Series: Pharmacology and Toxicology: Basic and Clinical Aspects Volume: 3, 2002), as the negative control (in FIG. 1, denoted by "Negative"), the peptides of the 11 sequences selected in Example 1-1 were evaluated.

The peptides of the 11 sequences selected in Example 1-1 were synthesized by the solid phase method, and fluorescently labeled by coupling 5,6-Carboxyfluorescein to the N-terminus of each peptide. Furthermore, the peptides were purified by HPLC to obtain a purity of 70% or more. Subsequently, each fluorescently labeled peptide was dissolved in 10% Dimethyl Sulfoxide (DMSO) to obtain 1 mM (hereinafter referred to as peptide solution).

Three kinds of cells were used for incorporating the peptides: CHO cells (ATCC NO. CCL-61), HeLa cells, and Jurkat cells. $10^4$ CHO cells and HeLa cells and $10^5$ Jurkat cells were separately inoculated to a 96-well plate, and cultured for 2 or 3 days. Subsequently, when the cells became confluent, each peptide solution was added to each type of cell, and the cells were incubated for 1 hour. After each type of cell was washed with PBS three times, 100 µL of 0.25% trypsin-1 mM EDTA solution was added, and trypsinization was performed at room temperature for 5 minutes. After 400 µL of PBS (10% FCS) was added to neutralize the trypsin, the cells were washed with 1 mL of HBSS (Hanks' Balanced Salt Solution/produced by Invitrogen) three times. After the washing, the cells were suspended in 50 µL of HBSS and analyzed using a confocal microscope. Measurements and analysis were performed using a confocal differential interference laser microscope system (Bio-Rad, Radience2100/Green He—Ne, 488 nm, microscope: Nikon, ECLIPSE E600).

As a result, the peptide of the novel PTD candidate sequence shown by SEQ ID NO:33 in the sequence listing (in FIG. 1 to FIG. 3, denoted by "KSH1") exhibited the highest intracellular transferability. The results for the KSH1 peptide, positive control and negative control are shown in FIG. 1. In all of the CHO cells, HeLa cells and Jurkat cells, fluorescence from the KSH1 peptide was observed. The fluorescence intensity from the KSH1 peptide was higher than the fluorescence intensity of the positive control. Furthermore, the intracellularly transported peptide was not localized, but detected both in the nucleus and in cytoplasm.

From these results, the KSH1 peptide was found to translocate into cells. It was also found that the amount thereof exceeded that of the HIV-derived TAT peptide, a conventionally known PTD.

Furthermore, CHO cells were inoculated to a slide chamber (produced by Nunc), 25 µM of each of the KSH1 peptide and positive control was added to the CHO cells, and the intracellular transferability thereof was determined using a confocal microscope.

Figure 2:
FIG. 2 A representation showing results of an intracellular translocation test of a fluorescence-labeled peptide using a slide chamber. The upper panels of photographs show fluorescence from FITC; the lower panels show differential interference microscopic images of cells in combination with fluorescence images.
Figure 2:

The results are shown in FIG. 2.

From these results, it was found that the KSH1 peptide was translocated into all CHO cells.

Example 1-3

Flowcytometry Analysis

Each peptide solution, adjusted to 1 mM, was diluted with a medium to three levels, 100 µM, 50 µM, and 25 µM, and added to cells. Three kinds of cells were used: CHO cells, HeLa cells, and Jurkat cells. After each peptide solution was added, the cells were incubated for 1 hour. After the cells were washed with PBS three times, 100 µL of 0.25% trypsin-1 mM EDTA solution was added, and trypsinization was performed at room temperature for 5 minutes. After 400 µL of PBS (10% FCS) was added to stop the trypsinization, the cells were washed with 1 mL of HBSS three times. After the washing, the cells were suspended in 500 µL of PBS (10% FCS) and subjected to flowcytometry (hereinafter, FACS) analysis using FACS Calibur (Becton Dickinson).

Figure 3:
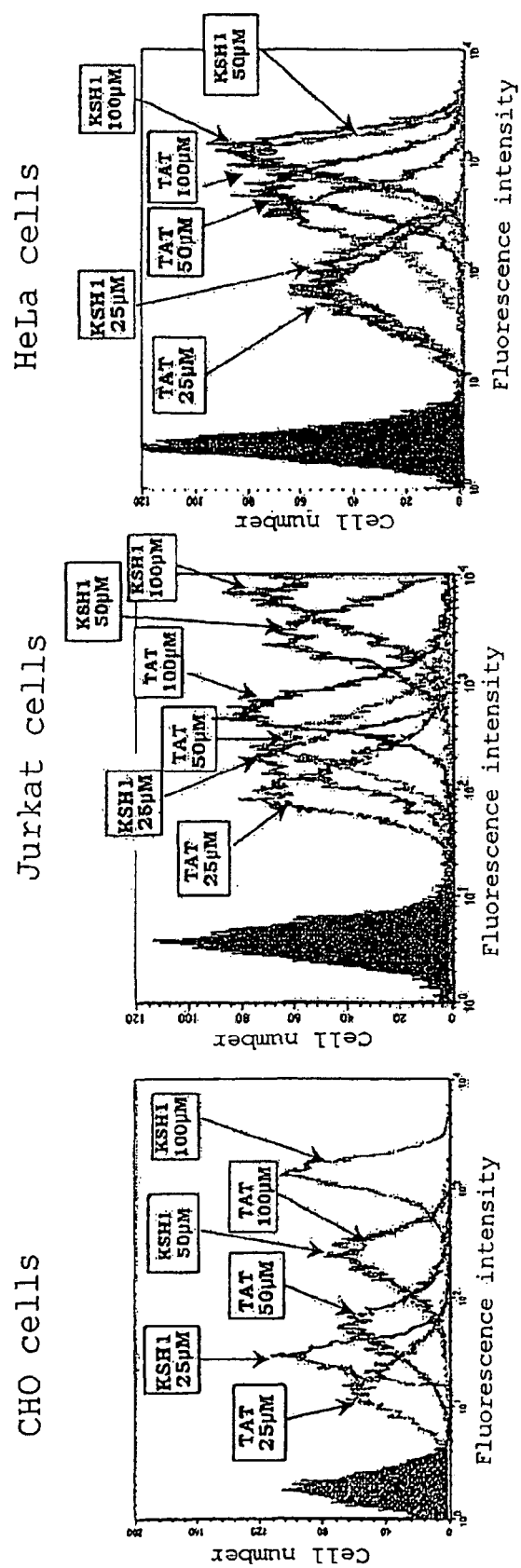
FIG. 3 A representation showing results of analyses by flowcytometry.

The results are shown in FIG. 3. The ordinate indicates cell number; the abscissa indicates fluorescence intensity.

From these results, it was found that the KSH1 peptide exhibited 3 to 10 times higher intracellular transferability than the positive control, having a potent capability of translocation.

Example 2

Confirmation of Translocation Activity Using eGFP Fusion Protein

Example 2-1

Construction of His-eGFP Expression Vector

With an eGFP cDNA (eGFP-NII) (produced by Amersham Pharmacia) as the template, "a His-eGFP expression vector" having a His-Tag and restriction endonuclease recognition sites was constructed by a PCR method.

PCR was performed using the Easy-A PCR kit (produced by Stratagene). An eGFP cDNA (eGFP-NII) DNA for the template was diluted to 200 ng/mL. Synthetic DNAs for the primers were adjusted to 20 µM. The template, the Fw primer, and the RV primer, each 1 µl, 10 µl of Easy-A PCR buffer, 8 µL of dNTPs (2.5 mM), and 0.5 µL of Easy-A were mixed, and this mixture was filled up with sterile distilled water to make 100 µL. PCR amplification conditions were as follows: 94° C. for 2 minutes, 1 cycle; and 94° C. for 30 seconds, 60° C. for 30 seconds and 72° C. for 2 minutes, 30 cycles.

Here, the PCR was performed using the Fw primer shown by SEQ ID NO:116 in the sequence listing (Nco-His-GFP-f) and the Rv primer shown by SEQ ID NO:117 in the sequence listing (GFP-Rev-Bam).

Next, for cloning into a vector, the PCR-amplified fragment was digested with the restriction endonucleases NcoI and BamHI, and a 0.8-kb DNA fragment recovered. The recovered DNA fragment was inserted into pET14b. The thus-constructed "His-eGFP expression vector" is a vector wherein the His-eGFP fusion protein is expressed under the control of the T7 promoter.

Example 2-2

Construction of His—Novel PTD Candidate Sequence—eGFP Expression Vector

By a PCR method, with an eGFP cDNA (eGFP-NII) as the template, "a His-KHS1-eGFP expression vector" having a His-Tag, a novel PTD candidate sequence and restriction endonuclease recognition sites was constructed.

PCR was performed using the Fw primer shown by SEQ ID NO:118 in the sequence listing (KSH-kp-nd-GF-f) and the Rv primer shown by SEQ ID NO:117 in the sequence listing (GFP-Rev-Bam). Further PCR was performed with the amplified fragment as the template, using the Fw primer shown by SEQ ID NO:119 in the sequence listing (KSH-kp-nd-f2) and the Rv primer shown by SEQ ID NO:117 in the sequence listing (GFP-Rev-Bam).

Subsequently, for cloning into a vector, the PCR-amplified fragment was digested with the restriction endonucleases NcoI and BamHI, and a 0.8-kb DNA fragment was recovered. The recovered DNA fragment was inserted into pET14b.

The thus-constructed "His-KHS1-eGFP expression vector" has the His-KSH1-eGFP fusion protein expressed under the control of the T7 promoter.

Example 2-3

Preparation of eGFP Fusion Proteins

After the BL21LysS strain, derived from *Escherichia coli* strain B, was transformed with the "His-eGFP expression vector" and the "His-KSH1-eGFP expression vector" constructed in Examples 2-1 and 2-2, respectively, each transformant was precultured in 20 mL of LB (37° C., 15 hours).

The preculture broth was inoculated to 1 L of LB at 2%, and cultured at 37° C. for 2.5 hours. IPTG was added at a final concentration of 1 mM, and further cultivation was performed for 4 hours. After centrifugation (4000 rpm, 20 min Hitachi himac CR7) and bacterial cell collection, the bacterial cells were suspended in 50 mL of PBS. Furthermore, the suspension was centrifuged (3500 rpm, 20 min KUBOTA 5200), and bacterial cells were collected. Subsequently, the bacterial cells were suspended in 30 mL of PBS and freeze-thawed three times. After addition of 15 µL of DNase solution (Benzonase Takara Bio NV677) and bacterial cell incubation at room temperature for 10 minutes, centrifugation was performed (18000 rpm, 20 min TOMY UD-201), and the supernatant was recovered. The supernatant was applied to a PBS-equilibrated Ni-NTA column (QIAGEN 30430). After the column was washed with 50 mL of a PBS containing 10 mM imidazole, the fusion proteins were eluted with 4 mL of a PBS containing 200 mM imidazole. 15 μL of the eluate was electrophoresed by SDS-PAGE (PAG-Mini, 4-20% gradient gel, Daiichi Pure Chemicals), the gel after electrophoresed was stained using Quick CBB (Wako Pure Chemical Industries, 299-50101), and detection of proteins was attempted.

As a result, bands with desired sizes corresponding to the His-KSH1-eGFP fusion protein and the His-eGFP fusion protein were detected.

Example 2-4

Confirmation of Intracellular Translocation of KSH1 Fusion Protein

An intracellular translocation test of each fusion protein was performed using CHO cells.

CHO cells or HeLa cells were inoculated to a 96-well plate at $10^4$ cells per well; 2 days later, the cells were used after becoming confluent. After the cells were washed with MEM medium three times, a peptide solution comprising the His—novel PTD candidate sequence—eGFP fusion protein and a peptide solution comprising the His-eGFP fusion protein, each 100 μL, was added, and the cells were incubated at 37° C. for 1 hour. After the cells were washed with PBS three times, the cells were recovered via trypsinization. After the recovered cells were washed with MEM medium one time, and with PBS (10% FCS) three times, the cells were suspended in 100 μL of PBS (10% FCS) and subjected to confocal microscopy.

As a result of the confocal microscopy, fluorescence from eGFP was detected in the cells to which the peptide solution comprising the His—novel PTD candidate sequence—eGFP fusion protein had been added.

Figure 4:
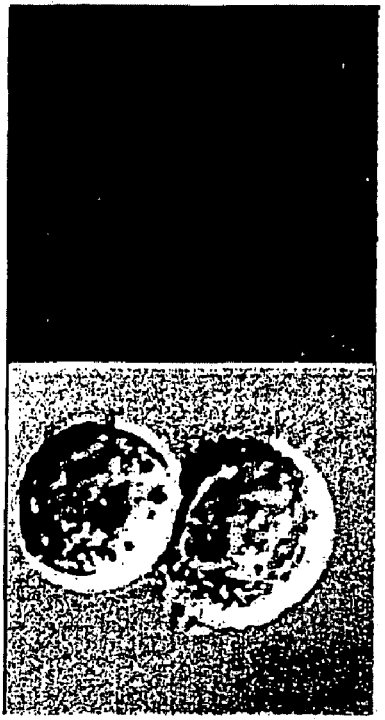
FIG. 4 A representation showing results of intracellular translocation tests of eGFP fusion proteins using a confocal microscope.
Figure 4:
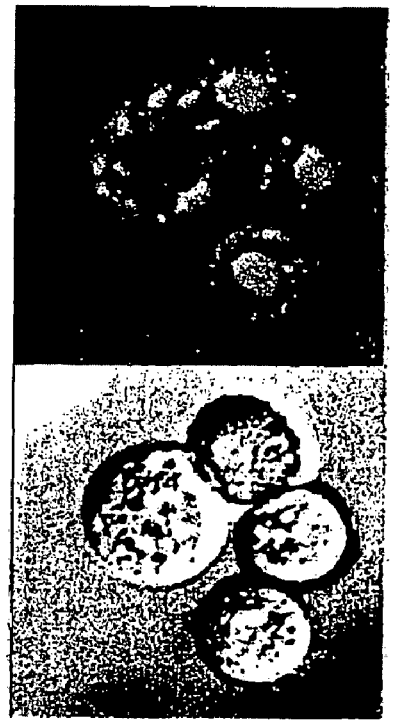
Figure 4:
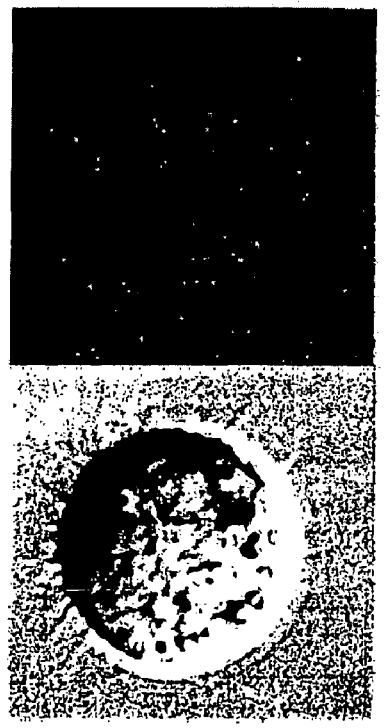
Figure 4:

The results are shown in FIG. 4.

From these results, it was found that the His—novel PTD candidate sequence—eGFP fusion protein (in FIG. 4, denoted by "KSH1") was translocated into the cells. Meanwhile, no translocation of His-eGFP (in FIG. 4, denoted by "His") into the cells was detected.

Furthermore, because the His—novel PTD candidate sequence—eGFP fusion protein was detected in a dot-by-dot pattern, its localization in endosome was demonstrated. This disagrees with the fact that the peptide alone is not localized in the cells as shown in Example 1-2. PTD fusion proteins have been reported to be incorporated into cells by macropinocytosis and localized in endosome (J Control Release. 2005 Jan. 20; 102(1):247-53 Cationic TAT peptide transduction domain enters cells by macropinocytosis. Kaplan I M, Wadia J S, Dowdy S F.). Hence, it was suggested that the novel PTD candidate sequence might penetrate the cell membrane by the same mechanism as other PTD peptides.

Example 3

Intracellular Translocation Test Using Synthetic Peptides of Modified PTD Sequences In the Examples and drawings below, the sequence identification numbers in the sequence listing corresponding to the names of the individual peptides are as shown in Table 1-1 and Table 1-2.

TABLE 1-1

| indication in Examples and Figures | SEQ ID NO: |
|---|---|
| KSH1-1 | 1 |
| KSH1-2 | 2 |
| KSH1-3 | 3 |
| KSH1-4 | 4 |
| KSH1-5 | 5 |
| KSH1-6 | 6 |
| KSH1-7 | 7 |
| KSH1-8 | 8 |
| KSH1-9 | 9 |
| KSH1-11 | 10 |
| KSH1-12 | 11 |
| KSH1-13 | 12 |
| KSH1-14 | 13 |
| KSH1-15 | 14 |
| KSH1-16 | 15 |
| KSH1-17 | 16 |
| KSH1-18 | 17 |
| KSH1-19 | 18 |
| KSH1-20 | 19 |
| KSH1-21 | 20 |
| KSH1-22 | 21 |
| KSH1-23 | 22 |
| KSH1-24 | 23 |
| KSH1-25 | 24 |
| KSH1-26 | 25 |
| KSH1-27 | 26 |

TABLE 1-2

| KSH1-28 | 27 |
|---|---|
| KSH1-29 | 28 |
| KSH1-30 | 29 |
| KSH1-33 | 30 |
| KSH1-34 | 31 |
| KSH1-35 | 32 |
| KSH1 | 33 |
| KSH1-36 | 34 |
| KSH3 | 35 |
| KSH4 | 36 |
| KSH5 | 37 |
| KSH6 | 38 |
| KSH7 | 39 |
| KSH8 | 40 |
| KSH9 | 41 |
| KSH10 | 42 |
| KSH2 | 43 |
| KSH2-1 | 44 |
| KSH2-2 | 45 |
| KSH2-3 | 46 |
| KSH2-4 | 47 |
| Positive or TAT | 50 |
| Negative | 51 |

Example 3-1

Analysis of KSH1-1 to KSH1-9

Figure 5:
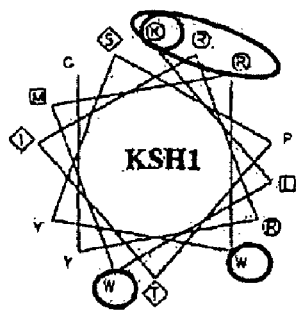
FIG. 5 A representation showing the wheel structures of the peptides KSH1 and KSH1-1 to 1-9 (SEQ ID NO: 33 and SEQ ID NOS: 1-9, respectively). In the drawings below, abbreviations for amino acids used in wheel structures are defined as follows: A: alanine, V: valine, L: leucine, I: isoleucine, P: proline, F: phenylalanine, W: tryptophan, M: methionine, G: glycine, S: serine, T: threonine, C: cysteine, Y: tyrosine, N: asparagine, Q: glutamine, E: glutamic acid, K: lysine, R: arginine, H: histidine, D: aspartic acid.
Figure 5:
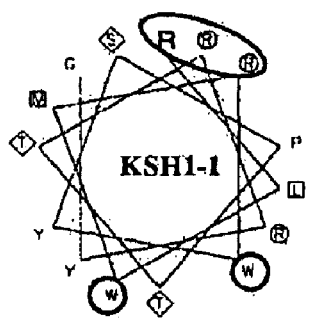
Figure 5:
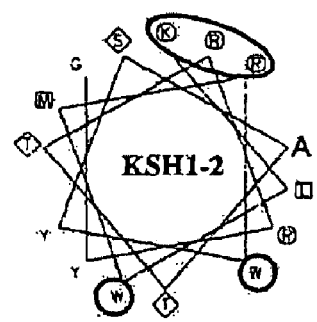
Figure 5:
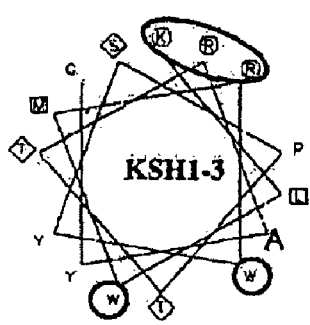
Figure 5:
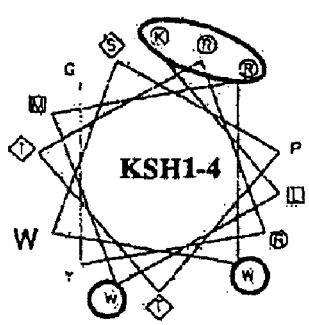
Figure 5:
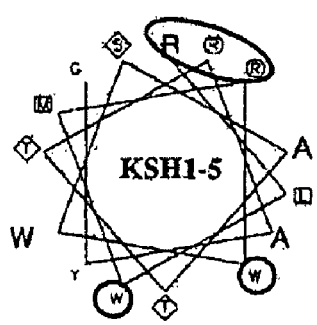
Figure 5:
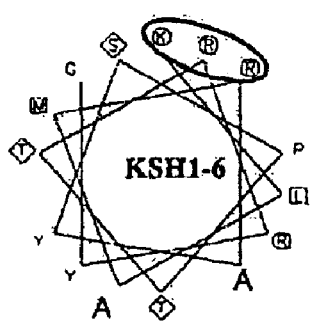
Figure 5:
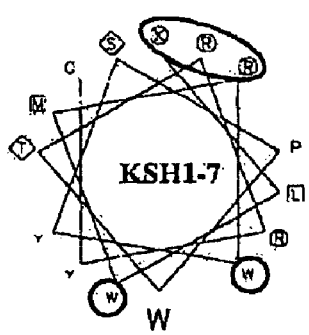
Figure 5:
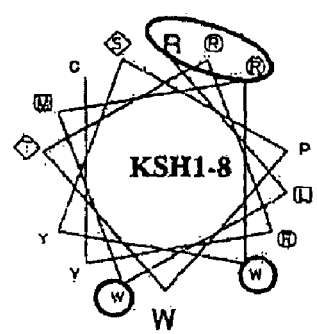
Figure 5:
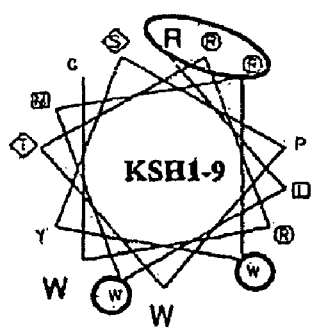
Figure 6:
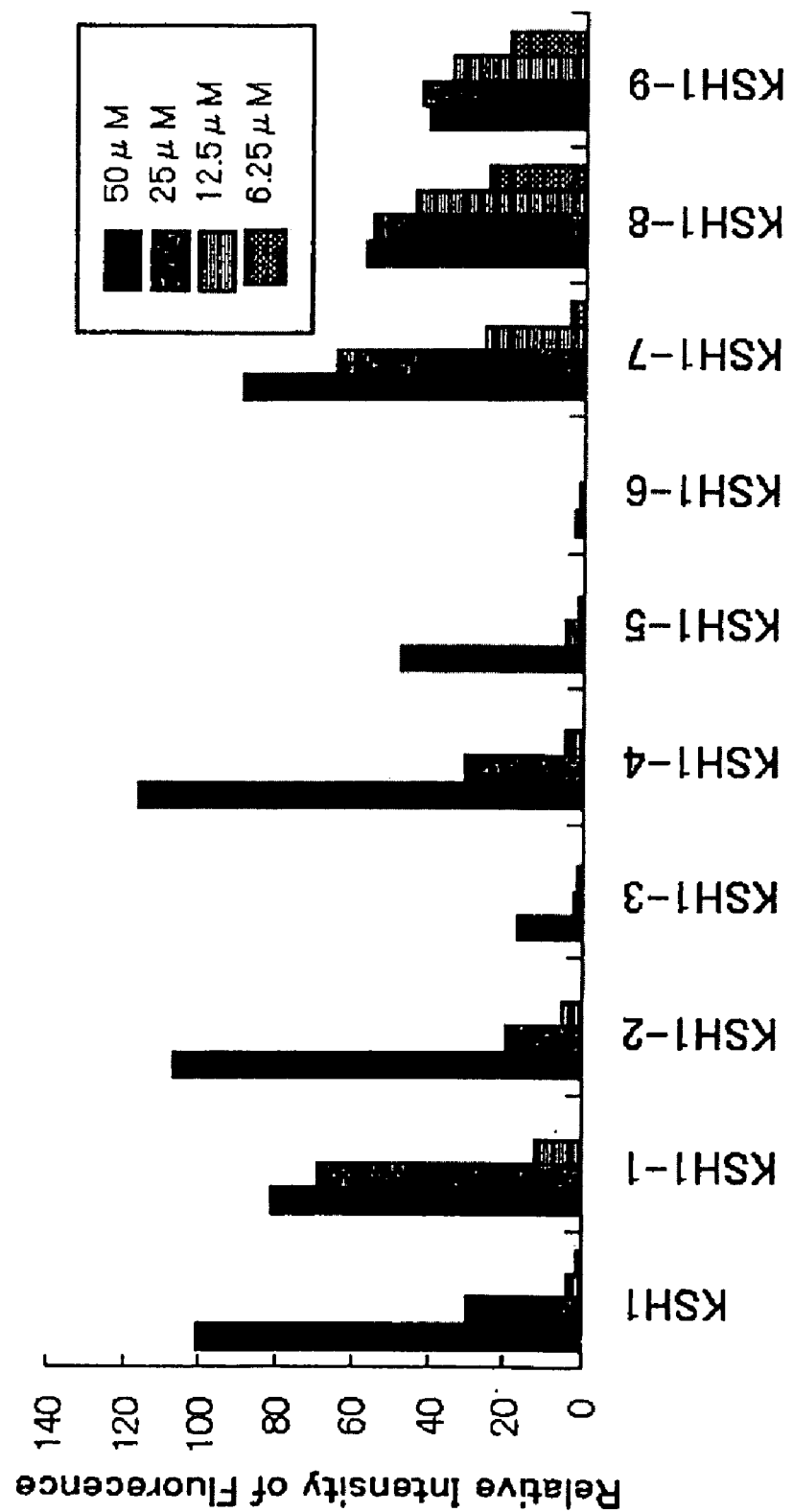
FIG. 6 A representation showing results of analyses of the fluorescence-labeled peptides KSH1 (SEQ ID NO: 33) and KSH1-1 to 1-9 (SEQ ID NOS: 1-9) in CHO cells by flow cytometry (FACS).

Wheel structure prediction (Trends Genet. 16(6): 276-7, 2000) of the primary sequence of the KSH1 peptide (SEQ ID NO:33 in the sequence listing) revealed characteristic findings of the formation of a lysine/arginine cluster, the presence of two tryptophans, the containment of proline, a rigid amino acid, and the presence of arginine at a position adjoining to tryptophan, though the arginine was not involved in the cluster formation. Hence, in order to determine the implication of these characteristic sequences in the intracellular translocation, SEQ ID NOS:1 to 9 in the sequence listing were designed (FIG. 5). Each peptide was synthesized, fluorescently labeled, purified and dissolved in the same manner as Example 1-2, a test of translocation into CHO cells was performed, and an evaluation was performed by confocal microscopic analysis and FACS. FACS analysis was performed in the same manner as Example 1-3. For the KSH1 peptide and modified PTD sequences, i.e., KSH1-1 to KSH1-9 peptides (SEQ ID NOS:1 to 9 in the sequence listing), fluorescence intensities determined by FACS analysis are shown in FIG. 6. The peptide addition concentrations were 50 µM, 25 µM, 12.5 µM and 6.5 µM.

When the lysine of the lysine/arginine cluster was substituted with arginine (KSH1-1), at a concentration of 50 µM, the translocation efficiency decreased by about 20% compared with KSH1; however, when the peptide concentration was reduced, the intracellular translocation was accentuated compared with KSH1 (about 2 times at 25 µM, about 8 times at 12.5 µM, about 2 times at 6.25 µM). This demonstrated the importance of the lysine/arginine cluster.

Next, to examine the role of the arginine not involved in the cluster formation, out of the three arginines being present in KSH1, the arginine was substituted with alanine. When the arginine was substituted with alanine, the intracellular translocation decreased remarkably, with intracellular translocation detected only at 50 µM (KSH1-3). It was found that this arginine existing in the vicinity of tryptophan plays an important role in the intracellular translocation.

To examine the significance of proline, which is thought to influence the conformation of peptides, proline was substituted with alanine; no influence on the intracellular transferability was observed (KSH1-2).

Tryptophan is an amino acid characteristic of KSH1, and there are two tryptophans located at the poles of the lysine/arginine cluster on the wheel structure as sandwiching threonine. When the two tryptophans were both substituted with alanine, the intracellular translocation was no longer observable at all (KSH1-6). From this finding, it was found that tryptophan was important to the intracellular translocation.

Whether the intracellular transferability was changed by increasing the number of tryptophans was examined. When threonine was substituted with tryptophan to form a tryptophan cluster (KSH1-7), the intracellular transferability was accentuated remarkably. Compared with KSH1, not less than 3 times higher intracellular translocation was detected between 25 µM and 6.15 µM, and not less than 10 times higher intracellular translocation was detected at 12.5 µM. The accentuation of the transferability showed the same profile as KSH1-1. Meanwhile, even when three tryptophans were uniformly arranged on the wheel structure, the intracellular translocation did not change (KSH1-4). From this finding, it was thought that the intracellular transferability was accentuated because of the formation of the tryptophan cluster.

Since the transferability was accentuated by forming the tryptophan cluster, and bearing in mind the results for KSH1-1, lysine was substituted with arginine (KSH1-8); the intracellular translocation at 50 µM decreased, but the translocation at 25 µM or less was accentuated. Since enlarging the tryptophan cluster was expected to accentuate the intracellular translocation, the number of tryptophans was increased to 4 (KSH1-9), but the same tendency as KSH1-8 was obtained.

Example 3-2

Analysis of KSH1-11 to 1-23 and KSH1-35

Figure 7:
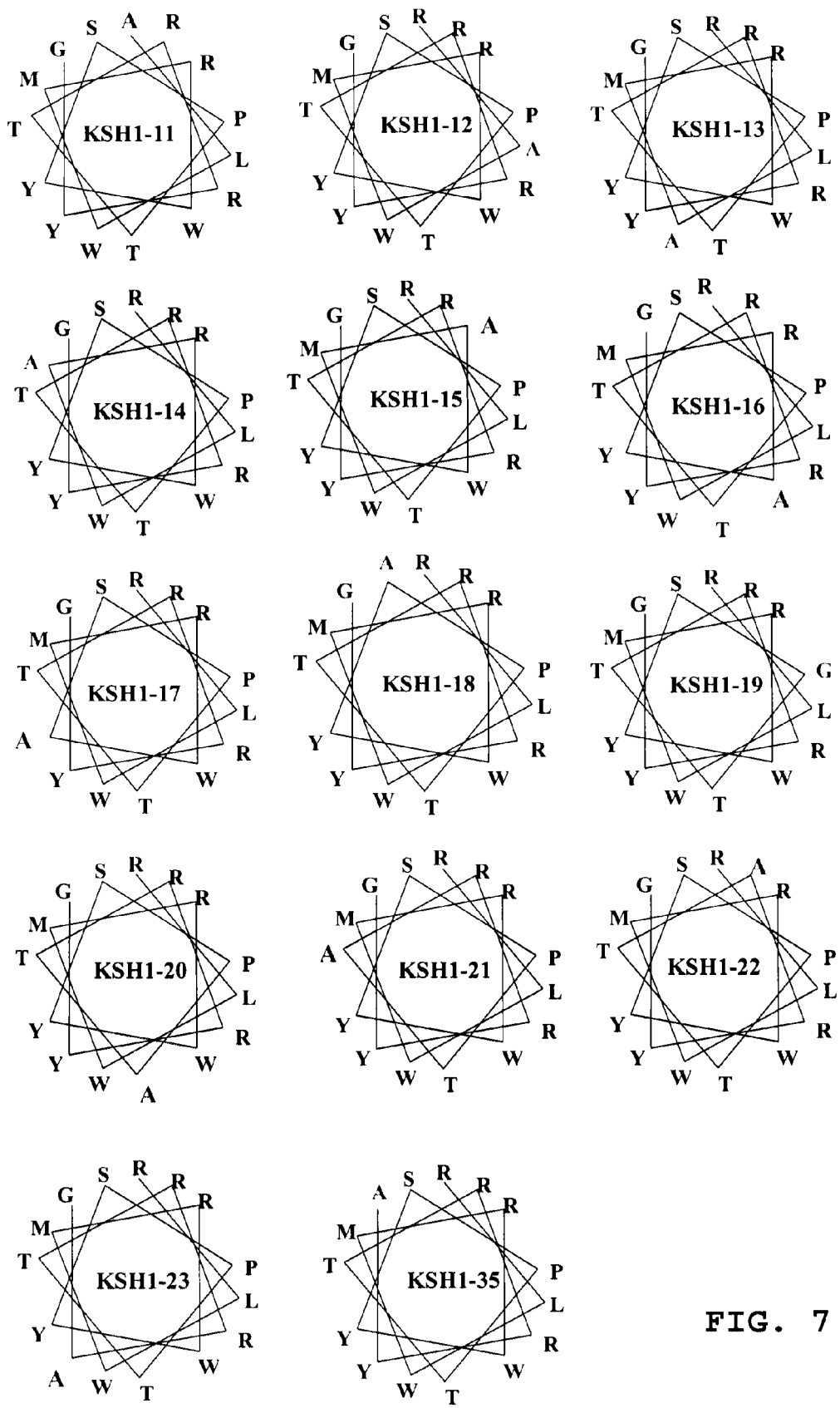
FIG. 7 A representation showing the wheel structures of the peptides KSH1-11 to 1-24 (SEQ ID NOS: 10-23) and KSH1-35 (SEQ ID NO: 32).
Figure 8:
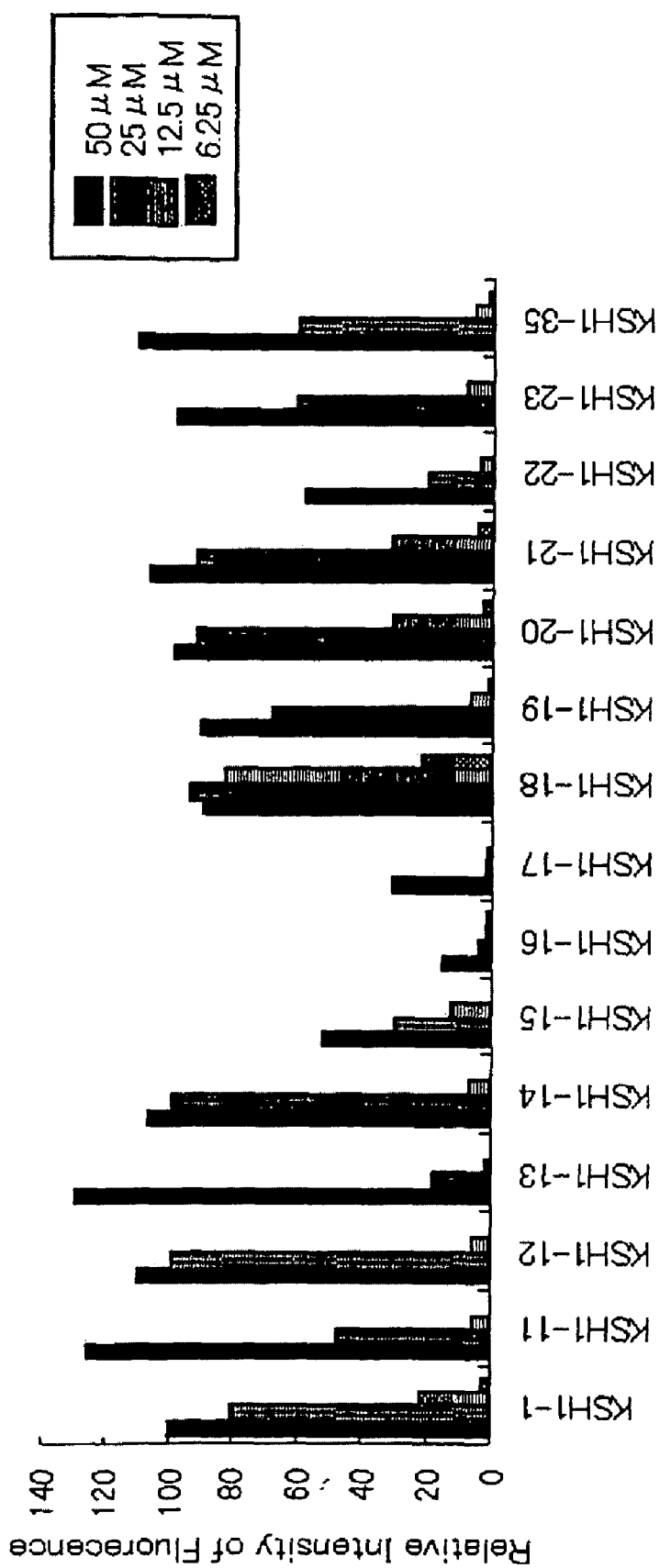
FIG. 8 A representation showing results of analyses of the fluorescence-labeled peptides KSH1-11 to 1-24 (SEQ ID NOS: 10-23) and KSH1-35 (SEQ ID NO: 32) in CHO cells by flowcytometry.

To determine which amino acids are important to the intracellular translocation, comprehensive alanine substitution was performed on the basis of KSH1-1 to design KSH1-11 (SEQ ID NO:11 in the sequence listing) to KSH1-23 (SEQ ID NO:22 in the sequence listing) and KSH1-35 (SEQ ID NO:32 in the sequence listing) (FIG. 7). Each peptide was synthesized, fluorescently labeled, purified and dissolved in the same manner as Example 1-2, a test of translocation into CHO cells was performed, and an evaluation was performed by confocal microscopic analysis and FACS. FACS analysis was performed in the same manner as Example 1-3. For KSH1 and modified PTD sequences, i.e., KSH11-11 to 23 and KSH1-35, fluorescence intensities determined by FACS analysis are shown in FIG. 8. The peptide addition concentrations were 50 µM, 25 µM, 12.5 µM and 6.5 µM.

When arginine and tryptophan were substituted with alanine, the intracellular translocation decreased clearly. When the 7th tyrosine was substituted with alanine, almost no intracellular translocation was observed (KSH1-17); it was found that the 7th tyrosine was important to intracellular translocation. Even when the 1st arginine was substituted with alanine, the intracellular translocation did not decrease a lot (KSH1-11). When other arginines were substituted with alanine, the intracellular translocation decreased (KSH1-15 and KSH 1-22); however, compared with the 13th arginine substituted (KSH1-3), the reduction in the intracellular translocation was minor.

Regarding tryptophan, the 6th tryptophan was more important to the intracellular translocation than the 3rd (KSH1-13, KSH1-6). From these findings, it was thought that the 13th arginine, the 6th arginine and the 7th tyrosine played an important role in the intracellular translocation, and that other amino acids made a minor contribution to the intracellular translocation (KSH)-11, KSH1-12, KSH1-14, KSH1-19, KSH1-20, KSH1-23, KSH1-35).

The only case where alanine substitution accentuated the intracellular translocation was the substitution of the 8th serine with alanine.

Example 3-3

Analysis of KSH1-24 to 1-26 and KSH1-28 to 1-30

Figure 9:
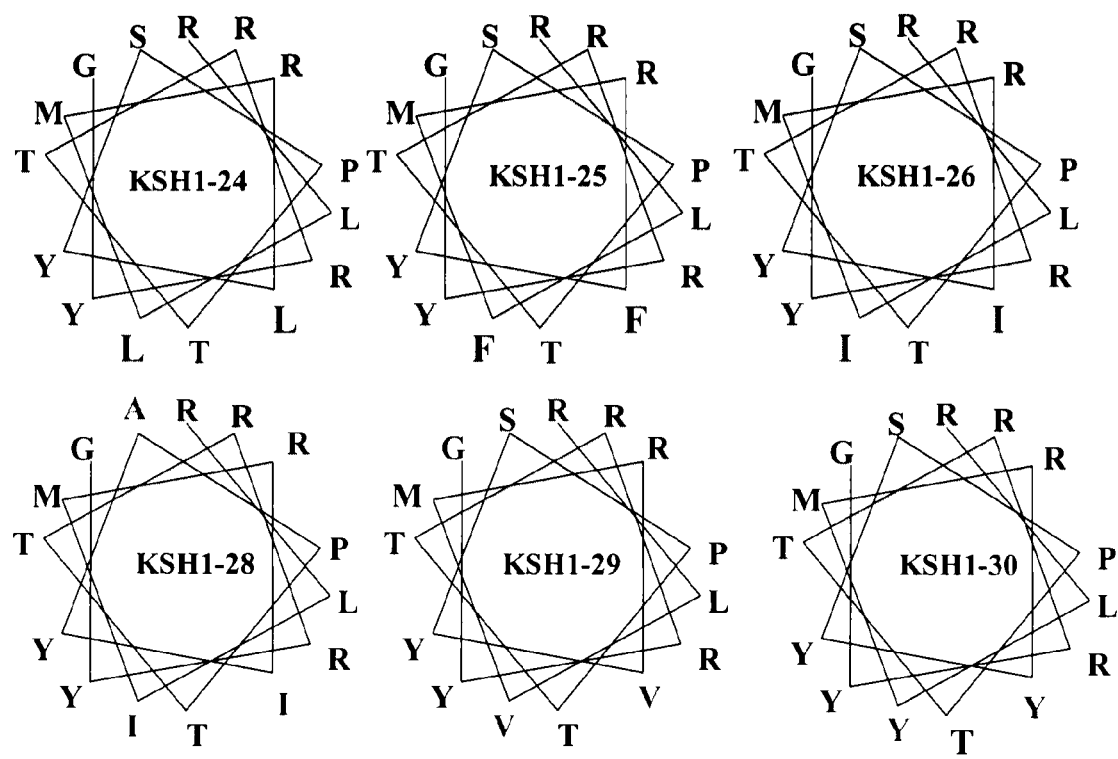
FIG. 9 A representation showing the wheel structures of the peptides KSH1-24 to 1-26 (SEQ ID NOS: 23-25) and KSH1-28 to 1-30 (SEQ ID NOS: 27-29).

In an attempt to substitute two tryptophans with other hydrophobic amino acids, KSH11-24 (SEQ ID NO:23 in the sequence listing) to KSH1-26 (SEQ ID NO:25 in the sequence listing) and KSH1-28 (SEQ ID NO:27 in the sequence listing) to KSH1-30 (SEQ ID NO:29 in the sequence listing) were designed (FIG. 9).

Figure 10:
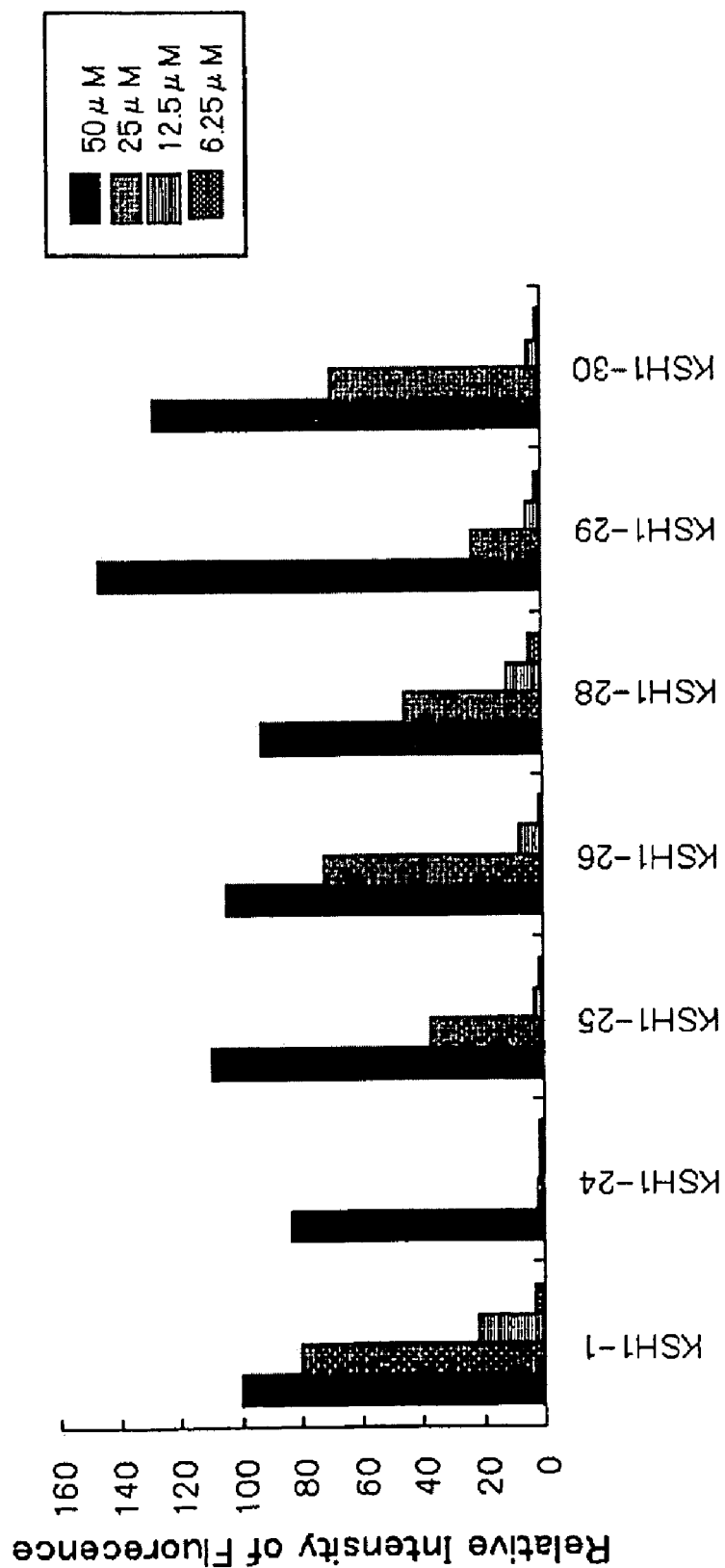
FIG. 10 A representation showing results of analyses of the fluorescence-labeled peptides KSH1-1, KSH1-24 to 1-26 (SEQ ID NOS: 23-25) and KSH1-28 to 1-30 (SEQ ID NOS: 27-M in CHO cells by flowcytometry.

Each peptide was synthesized, fluorescently labeled, purified and dissolved in the same manner as Example 1-2, a test of translocation into CHO cells was performed, and an evaluation was performed by confocal microscopic analysis and FACS analysis. FACS analysis was performed in the same manner as Example 1-3. For KSH1 and modified PTD sequences, i.e., KSH11-24 to 1-26 and KSH1-28 to 1-30, fluorescence intensities determined by FACS analysis are shown in FIG. 10. The peptide addition concentrations were 50 µM, 25 µM, 12.5 µM and 6.5 µM.

First, two tryptophans were substituted with leucine (KSH1-24), phenylalanine (KSH1-25) and isoleucine (KSH1-26); the intracellular translocation decreased with leucine, but was nearly the same as KSH1-1 with phenylalanine and isoleucine. Hence, with reference to KSH1-18, a modification was designed to substitute the 8th serine of KSH1-26 with alanine, but the intracellular translocation was accentuated very little.

Furthermore, two tryptophans were substituted with other hydrophobic amino acids, i.e., valine and tyrosine (KSH1-29, KSH1-30); the intracellular translocation decreased slightly with valine, but good intracellular translocation was exhibited with tyrosine. Summarizing these results for hydrophobic amino acids to substitute tryptophan, the intracellular translocation was better in the order of isoleucine, tyrosine, phenylalanine, valine, and leucine.

Example 3-4

Analysis of KSH1-27, KSH1-33, KSH1-34 and KSH1-36

Figure 11:
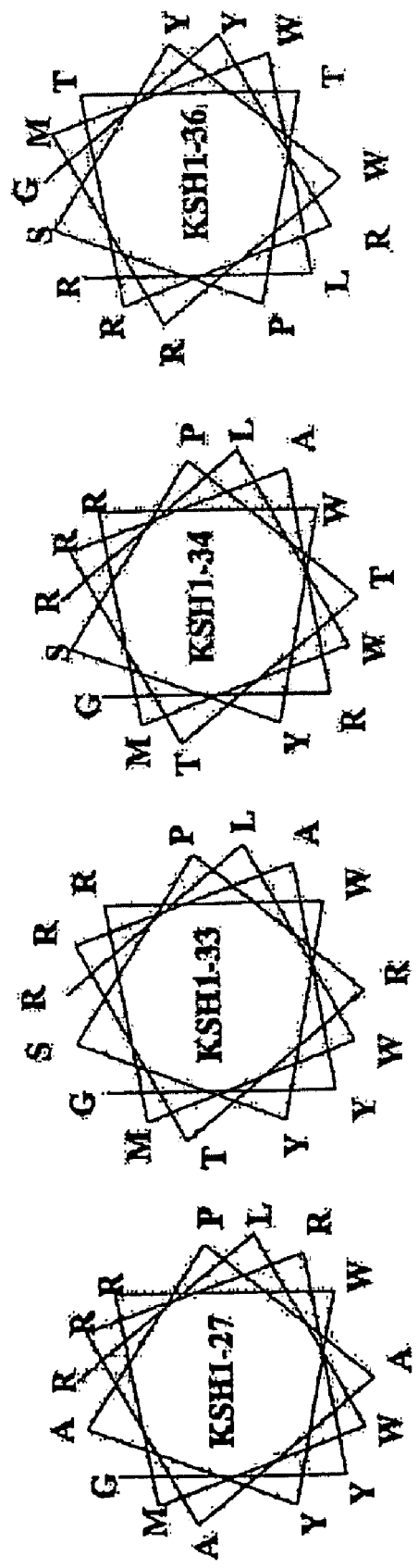
FIG. 11 A representation showing the wheel structures of the peptides KSH1-27 (SEQ ID NO: 26), KSH1-33 (SEQ ID NO: 30), KSH1-34 (SEQ ID NO: 31) and KSH1-36 (SEQ ID NO: 34).

KSH1-27 (SEQ ID NO:26 in the sequence listing), KSH1-33 (SEQ ID NO:30 in the sequence listing), KSH1-34 (SEQ ID NO:31 in the sequence listing) and KSH1-36 (SEQ ID NO:34 in the sequence listing) were designed (FIG. 11).

Figure 12:
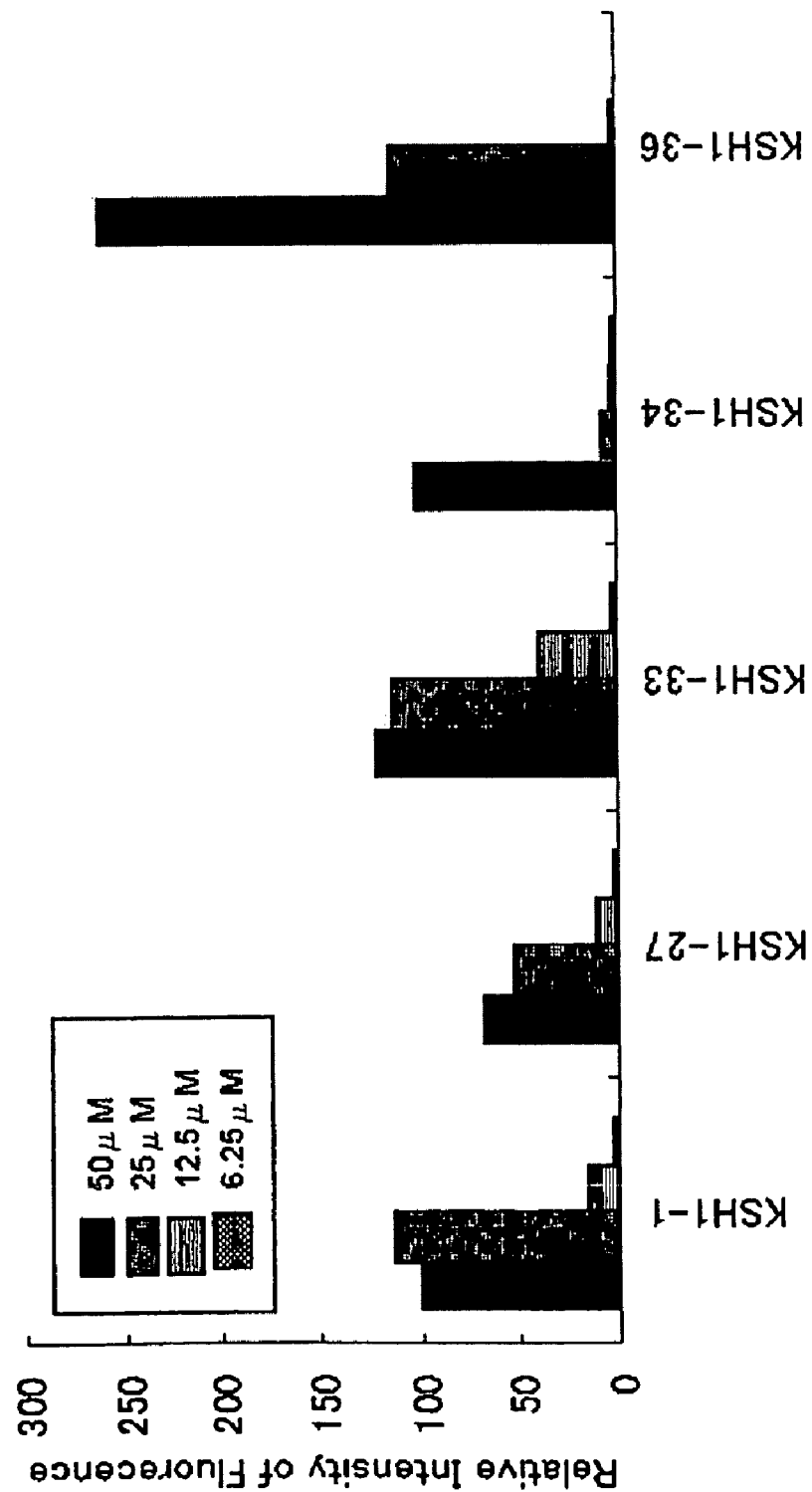
FIG. 12 A representation showing results of analyses of fluorescence-labeled peptides of KSH1-27 (SEQ ID NO: 26), KSH1-33 (SEQ ID NO: 30), KSH1-34 (SEQ ID NO: 31) and KSH1-36 (SEQ ID NO: 34) in CHO cells by flowcytometry.

Each peptide was synthesized, fluorescently labeled, purified and dissolved in the same manner as Example 1-2, a test of translocation into CHO cells was performed, and an evaluation was performed by confocal microscopic analysis and FACS analysis. FACS analysis was performed in the same manner as Example 1-3. For KSH1 and modified PTD sequences, i.e., KSH1-27, KSH1-33, KSH1-34 and KSH1-36, fluorescence intensities determined by FACS analysis are shown in FIG. 12. The peptide addition concentrations were 50 µM, 25 µM, 12.5 µM and 6.5 µM.

On the basis of the results for KSH1-18, serine and threonine were all substituted with alanine (KSH1-27); compared with KSH1-1, the intracellular translocation decreased slightly, but the translocation at low concentrations was nearly the same.

In KSH1-3, when the arginine (13th) existing in the vicinity of the 6th tryptophan on the wheel structure was substituted with alanine, the intracellular translocation became observable very little. Hence, to determine which position of arginine is important in KSH1-33, in the vicinity of tryptophan on the wheel structure or at the 13th position, the 13th arginine was substituted with alanine, and the 10th threonine was substituted with arginine. As a result, the intracellular translocation was nearly equivalent or more than KSH1-1 in Table 1-1. From this finding, it was concluded that the presence of arginine in the vicinity of the 6th tryptophan on the wheel structure was important.

Furthermore, to determine whether the 13th arginine is no longer necessary if arginine is present in the vicinity of the 3rd tryptophan in KSH1-34, the 14th tyrosine existing in the vicinity of the 3rd tryptophan on the wheel structure was substituted with arginine. As a result, the intracellular translocation decreased considerably; it was concluded that the presence of arginine in the vicinity of the 6th tryptophan on the wheel structure was essential to the intracellular translocation.

KSH1-36, the reversed-chain peptide of KSH1, exhibited accentuated intracellular translocation at high concentrations compared with KSH1, but the intracellular translocation conversely tended to decrease at low concentrations.

Example 3-5

Intracellular Translocation Experiments in HeLa Cells and Jurkat Cells

In HeLa cells as with CHO cells, intracellular translocation experiments of synthetic peptides of modified PTD sequences were performed by confocal microscopic analysis. Compared with CHO cells, the intracellular translocation was generally lower, but the tendency was nearly the same as CHO cells. However, in HeLa cells than in CHO cells, the intracellular translocation of KSH1-7 was lower, and conversely the intracellular translocation of KSH1-16 was slightly higher. In conclusion, better intracellular translocation in HeLa cells was observed in the modified peptides KSH1-1, KSH1-8, KSH1-9, KSH1-18, KSH1-20 and KSH1-33.

In Jurkat cells as well, intracellular translocation experiments of synthetic peptides of modified PTD sequences were performed by confocal microscopic analysis. Compared with CHO cells, the intracellular translocation was generally considerably lower, but the tendency was nearly the same as CHO cells and HeLa cells. However, when tryptophan was substituted with other hydrophobic amino acids, the intracellular translocation decreased considerably. In conclusion, better intracellular translocation in Jurkat cells was observed in the modified peptides of SEQ ID NOS:KSH1-1, KSH1-7, KSH1-8, KSH1-9, KSH1-12, KSH1-14, KSH1-18, KSH1-20, KSH1-21 and KSH1-33 in the sequence listing, as compared to that of SEQ ID NO:37 in Tables 1-1 and 1-2.

Figure 13:
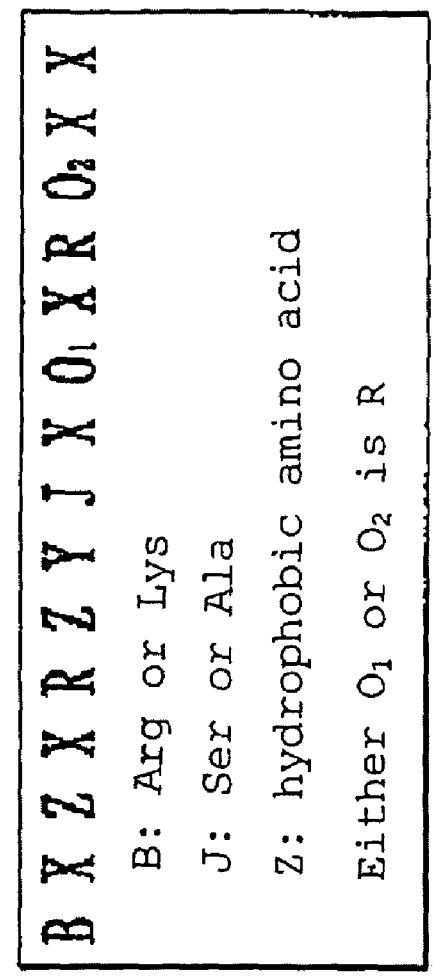
FIG. 13 A representation showing the wheel structure of a peptide of an amino acid sequence obtained from results of an investigation of a modification of the peptide KSH1.
Figure 13:
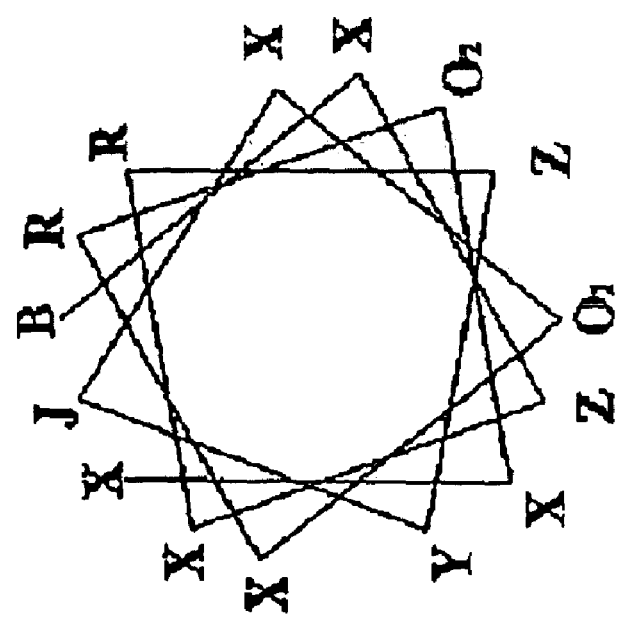

From the results of Examples 3-1 to 3-5, the sequences shown in FIG. 13 were identified. In the figure, B is arginine or lysine, either $O^1$ or $O^2$ is arginine, Z is a hydrophobic amino acid, J is serine or alanine, and X is an arbitrarily chosen amino acid.

Example 4

Intracellular Translocation Test of Modified PTD Sequences and eGFP Fusion Proteins in CHO Cells Example 4-1

Construction of eGFP Fusion Protein Expression Vector

In evaluating intracellular translocation using eGFP fusion proteins, two kinds of inserts (types C and D in FIG. 14) were prepared.

Primers for insert amplification were designed to allow the in-frame addition of a His-Tag and a PTD sequence to the N-terminus or C-terminus of eGFP. The design was such that the GGGS (SEQ ID NO: 120) or GGGSS (SEQ ID NO: 121) linker would be encoded in front and back of the His-Tag and the PTD sequence, respectively. The PTD sequence used was a DNA sequence that encodes PTD1 derived from HIV TAT. Furthermore, the DNA sequence portions of the GGGS (SEQ ID NO: 120) and GGGSS (SEQ ID NO: 121) linkers that encode the PTD moiety were prepared to produce recognition sequences for the restriction endonucleases BamHI and XhoI, respectively.

Figure 14:
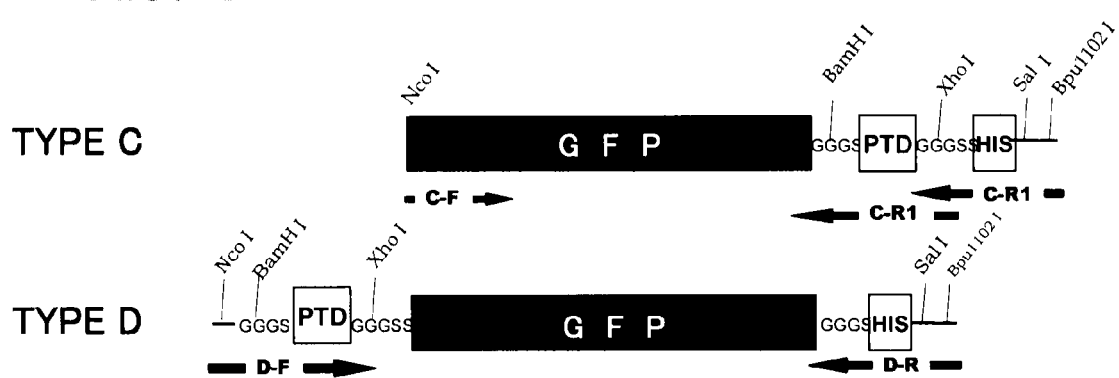
FIG. 14 A representation showing construct of the expression of eGFP fusion proteins. The depicted linker sequences GGGS and GGGSS are respectively described by SEQ ID NOS: 120 and 121.

Primer Design
Insert configuration C (type C in FIG. 14)

```
Forward primer C-F
            (SEQ ID NO: 52 in the sequence listing)
5'-GCC ATG GTG AGC AAG GGC GAG GAG CTG TTC-3'

Reverse primer C-R1
            (SEQ ID NO: 53 in the sequence listing)
5'-CAC CGC GGC GAC GTT GTC GTC GTT TCT TCC TGC CGT
AGG ATC CCC CTC CCT TGT ACA GCT CGT CCA TGC C-3'

Reverse primer C-R2
            (SEQ ID NO: 54 in the sequence listing)
5'-CGC TCA GCG TCG ACT CAC CCG TGA TGA TGG TGG TGA
TGA CTC GAG CCG CCA CCG CGG CGA CGT TGT CGT-3'
```

Insert configuration D (D type in FIG. 14)

```
Forward primer D-F
        (SEQ ID NO: 55 in the sequence listing)
5'-AAG CCA TGGGAG GGG GATCCT ACG GCA GGA AGA AAC
GAC GAC AAC GTC GCC GCG GTG GCG GCT CGA GTA TGG
TGA GCA AGG GCG AGG A-3'

Reverse primer D-R
        (SEQ ID NO: 56 in the sequence listing)
5'-CCG CTC AGC GTC GAC TCACCC GTG ATG ATG GTG GTG
ATG AGA ACC ACC ACC CTT GTA CAG CTC GTC CAT GCC-3'
```

Figure 15:
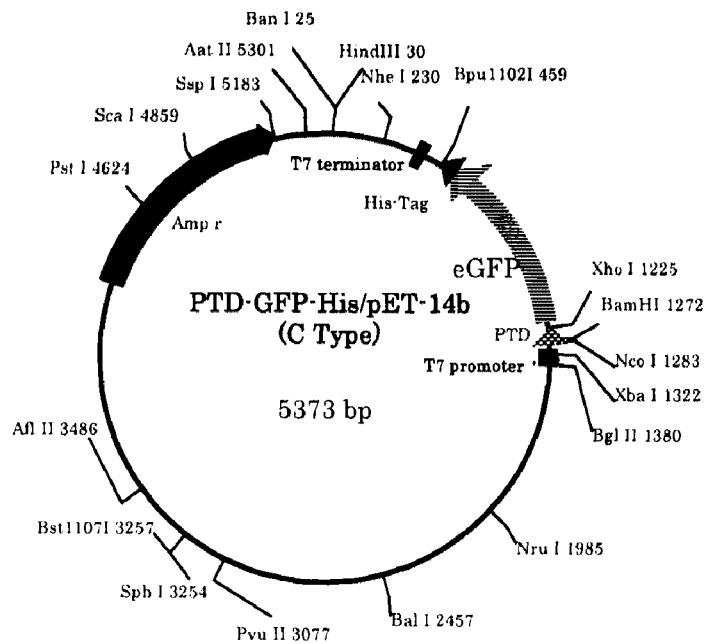
FIG. 15 Vector maps of eGFP fusion proteins.
Figure 15:
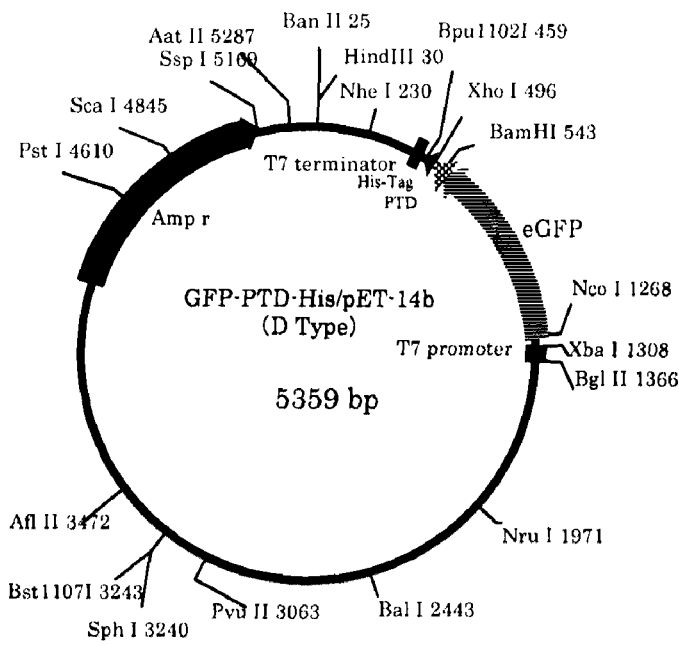

Thereby, it is possible to cleave the PTD moiety with BamHI and XhoI, and substitute the same with synthetic DNA. With eGFP as the template, the above-described SEQ ID NOS:52 to 56 in the sequence listing were inserted between the NcoI and Bpu1102I restriction endonuclease recognition sequences of pET14b (FIG. 15).

Figure 16:
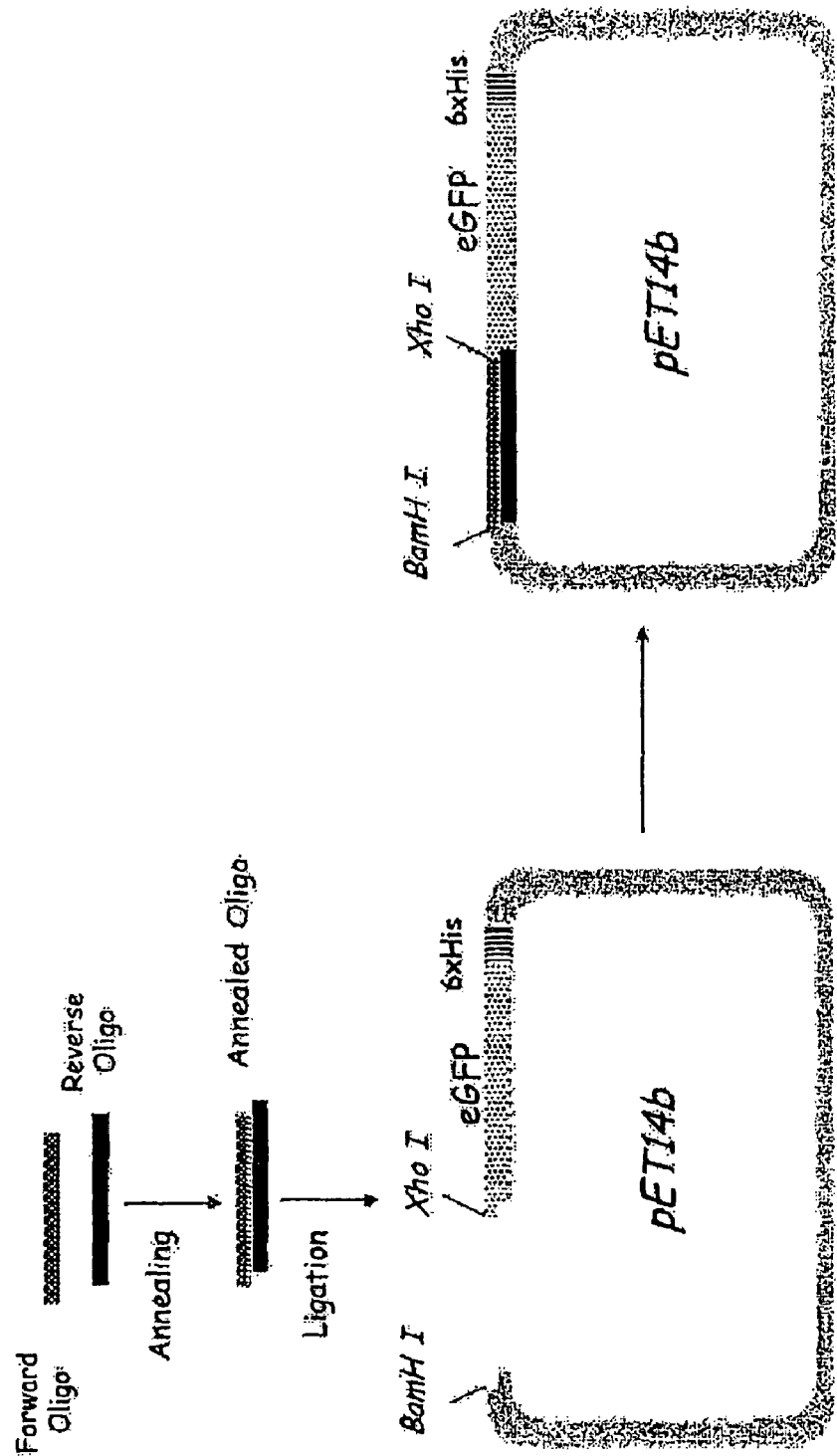
FIG. 16 A representation showing how to insert synthetic oligos into a vector. This drawing is for a type D vector.

The modified PTD sequences were inserted using the synthetic oligos shown in Table 2-1 and Table 2-2, by the method shown in FIG. 16.

TABLE 2-1

| name of modified PTD peptide | forward oligomer (F) or reverse oligomer (R) | SEQ ID NO: in the sequence listing |
|---|---|---|
| KSH1 | F | 58 |
|  | R | 59 |
| KSH1-1 | F | 60 |
|  | R | 61 |
| KSH1-2 | F | 62 |
|  | R | 63 |
| KSH1-3 | F | 64 |
|  | R | 65 |
| KSH1-4 | F | 66 |
|  | R | 67 |
| KSH1-5 | F | 68 |
|  | R | 69 |
| KSH1-6 | F | 70 |
|  | R | 71 |
| KSH1-7 | F | 72 |
|  | R | 73 |
| KSH1-8 | F | 74 |
|  | R | 75 |
| KSH1-9 | F | 76 |
|  | R | 77 |
| KSH1-11 | F | 78 |
|  | R | 79 |
| KSH1-13 | F | 80 |
|  | R | 81 |

TABLE 2-2

| KSH1-18 | F | 82 |
|---|---|---|
|  | R | 83 |
| KSH1-20 | F | 84 |
|  | R | 85 |
| KSH1-21 | F | 86 |
|  | R | 87 |
| KSH1-26 | F | 88 |
|  | R | 89 |
| KSH1-27 | F | 90 |
|  | R | 91 |
| KSH1-28 | F | 92 |
|  | R | 93 |
| KSH1-30 | F | 94 |
|  | R | 95 |
| KSH1-33 | F | 96 |
|  | R | 97 |
| KSH1-36 | F | 98 |
|  | R | 99 |

Used for negative control was one having H is alone added to the C-terminus, amplified using the primer set of SEQ ID NO:52 and 56 in the sequence listing with eGFP as the template.

After the BL21/LysS strain, derived from *Escherichia coli* strain B, was transformed with the constructed expression vector, each transformant was precultured in 20 mL of LB (37° C., 15 hours). The preculture broth was transplanted to 1 L of LB at 2%, and the transformant was cultured at 37° C. for 2.5 hours. IPTG was added at a final concentration of 1 mM, and further cultivation was performed for 4 hours. After centrifugation (4000 rpm, 20 min Hitachi himac CR7) and bacterial cell collection, the bacterial cells were suspended in 50 mL of PBS. Centrifugation (3500 rpm, 20 min KUBOTA 5200) was performed, and bacterial cells were collected. The bacterial cells were suspended in 30 mL of HBSS and freeze-thawed three times. DNase solution (Benzonase Takara Bio NV677), 15 µL, was added, and the bacterial cells were incubated at room temperature for 10 minutes. Centrifugation (18000 rpm, 20 min TOMY UD-201) was performed, and the supernatant was recovered. The supernatant was applied to an HBSS-equilibrated Ni-NTA column. After the column was washed with 50 mL of an HBSS containing 10 mM imidazole, the fusion proteins were eluted with 4 mL of an HBSS containing 200 mM imidazole.

Example 4-2

Intracellular Translocation of Modified PTD Sequences and eGFP Fusion Proteins in CHO Cells The intracellular translocation of fusion proteins was investigated using CHO cells. CHO cells were inoculated to a 48-well plate at $2 \times 10^4$ cells per well; the cells were used after becoming confluent. After the cells were washed with MEM medium three times, 150 µL of protein solution was added, and the cells were incubated at 37° C. for 3 hours. After plate washing with PBS three times, 0.25% trypsin/EDTA was added at 100 µL/well, an MEM medium containing 10% FCS was added at 400 µL/well, and the cells were recovered. After being washed with HBSS three times, the recovered cells were suspended in 100 µL of an HBSS containing 10% FCS, and subjected to confocal microscopy. The addition concentration was adjusted to obtain fluorescence intensities of $10^6$, $5 \times 10^5$, and $2.5 \times 10^5$ as determined by measuring the amount of eGFP-derived fluorescence (Ex485 nm/Em535 nm) using ARVO (Perkin-Elmer) (time span of measurement 1 second).

eGFP fusion proteins were prepared with KSH1-1, KSH1-7, KSH1-8, KSH1-9, KSH1-18 and KSH1-33, which exhibited clearly accentuated intracellular translocation compared with the KSH1 peptide in Example 3, as well as KSH1-20, KSH1-21, KSH1-26, KSH1-27, KSH1-28, KSH1-30 and KSH1-36. For analysis, type C fusion proteins were prepared for KSH1, KSH1-1, KSH1-7 and KSH1-8, and type D fusion proteins were prepared for the other peptides.

Figure 17:
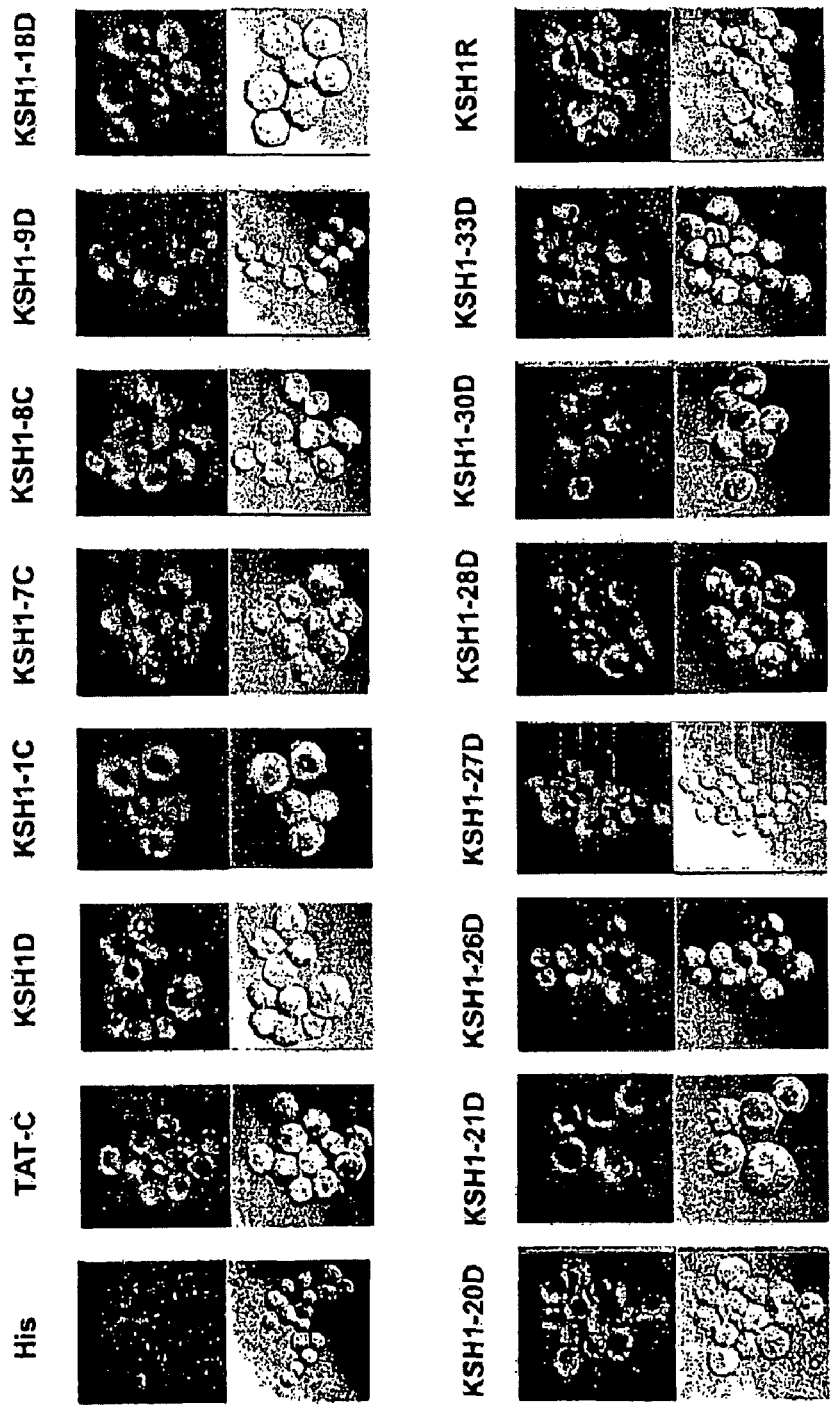
FIG. 17 A representation showing results of intracellular translocation tests of eGFP fusion proteins using a confocal microscope. The upper panels show fluorescence from FITC; the lower panels show differential interference microscopic images of cells in merged with fluorescence images.

For the prepared eGFP fusion proteins, an intracellular translocation test using CHO cells was performed; the results are shown in FIG. 17. The upper panels show the fluorescence of eGFP protein that had translocated into the cells; the lower panels show differential interference microscopic images of the cells in combination with fluorescence images. The fusion proteins were added to the cells after the fluorescence intensities thereof were uniformized to $10^6$. When fusion proteins of modified forms of KSH-1 exhibiting intracellular translocation and eGFP were added to CHO cells, fluorescence was detected in the cells; it was found that all modified forms of KSH-1 retained the capability of translocating fusion proteins into cells. Compared with the peptide alone, the fusion proteins showed smaller differences in translocation efficiency, but the fusion proteins with KSH1-1, KSH1-7 and KSH1-27 exhibited accentuated intracellular translocation compared with KSH1.

As the hydrophobicity of the peptide added increased, the intracellular translocation with fusion proteins showed an increased tendency not to reflect the results with the peptide. For KSH1-30, which had two tryptophans substituted with tyrosine, the intracellular translocated decreased considerably with fusion proteins despite that good results were obtained with the peptide; therefore, for substitution of two tryptophans, isoleucine (KSH1-26) was the most suitable.

For replacement of threonine and serine with alanine (KSH1-18, KSH1-20, KSH1-21), no clear accentuation of intracellular translocation was observed with fusion proteins. However, when all threonines and serines were substituted with alanine (KSH1-27), the intracellular translocation tended to be accentuated clearly; therefore, it was concluded that to change the intracellular translocation efficiency of fusion proteins, a larger structural change in the peptide moiety is required than the peptide alone.

In summary, with the addition of modified peptides of KSH1, proteins translocated into cells, but the translocation efficiency of fusion proteins differed from that of the peptide alone.

Example 5

Intracellular Translocation Test of Novel PTD Sequences (SEQ ID NOS:39 to 47 in the Sequence Listing)

Example 5-1

Selection of Novel PTD Sequences by FACS Analysis

The KSH1 peptide was a sequence obtained from a 7-time-concentrated library of Jurkat cells. Hence, 1000 IVVs contained in the 7-time-concentrated library of Jurkat cells were arbitrarily picked up, and the DNA sequences thereof were identified. Since analysis of KSH1 led to the anticipation that when the peptide sequence was applied to the wheel structure, the presence of a lysine/arginine cluster and tryptophan would be important, narrowing of 1000 sequences was performed with these conditions as criteria. As a result, 60 sequences met the criteria. Of the 1000 sequences, one kind of repeatedly appearing sequence was observed. For these sequences, fluorescently labeled peptides were synthesized, and their capabilities of translocation into cells were analyzed.

Each peptide was synthesized, fluorescently labeled, purified and dissolved in the same manner as Example 1-2, and an intracellular translocation test in CHO cells was performed by FACS analysis. Used for positive control were a PTD sequence derived from HIV TAT (SEQ ID NO:51 in the sequence listing) and the KSH1 peptide; used for negative control was a peptide sequence lacking intracellular transferability (SEQ ID NO:57 in the sequence listing).

Figure 18:
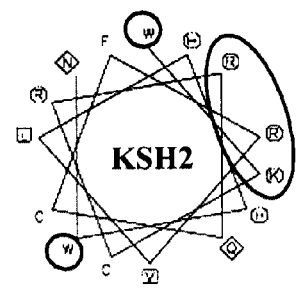
FIG. 18 A representation showing the wheel structures of the peptides KSH2 to KSH10 (SEQ ID NO: 43 and SEQ ID NOS: 35-42, respectively).
Figure 18:
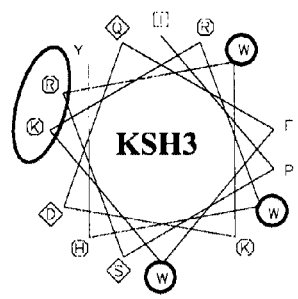
Figure 18:
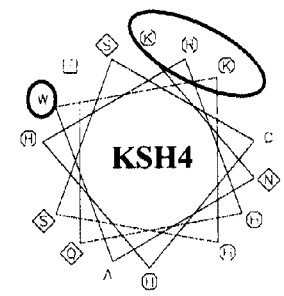
Figure 18:
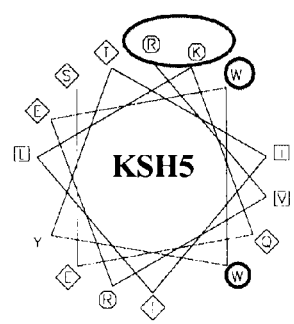
Figure 18:
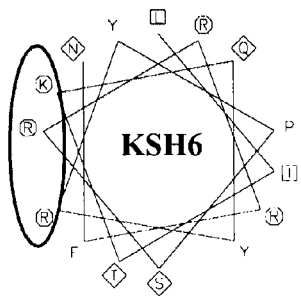
Figure 18:
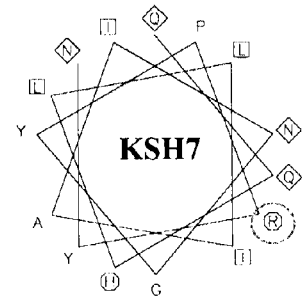
Figure 18:
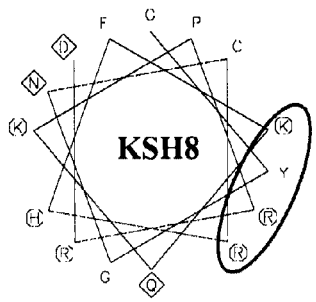
Figure 18:
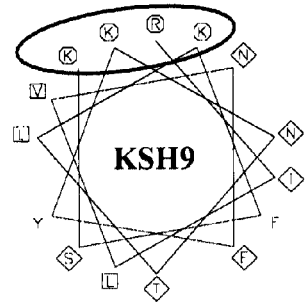
Figure 18:
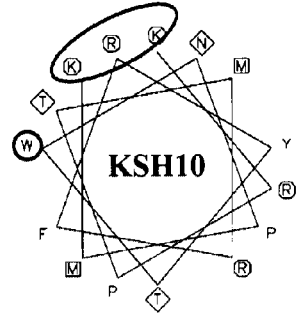

As a result of the FACS analysis, one kind of sequence exhibiting the same transferability as KSH1, and nine kinds of sequences exhibiting the same transferability as TAT-derived PTD, were identified in CHO cells. These nine kinds of peptide sequences are as shown by KSH3 to 10 and KSH2 (SEQ ID NOS:35 to 43 in the sequence listing) (FIG. 18).

Example 5-2

Cellular Transferability Analysis of Novel PTD Sequences by Confocal Microscopy

For KSH2 to KSH10 (SEQ ID NOS:35 to 43 in the sequence listing), a test of translocation into CHO cells was performed in the same manner as Example 1-2, and confocal microscopic analysis was performed. Used for positive control were a PTD sequence derived from HIV TAT (SEQ ID NO:50 in the sequence listing) and the KSH1 peptide; used for negative control was a peptide sequence lacking intracellular transferability (SEQ ID NO:57 in the sequence listing).

In the confocal microscopic analysis, a background correction was performed using cells to which the negative control peptide (SEQ ID NO:57 in the sequence listing) had been added. Thereafter, the positive control PTD1 peptide (SEQ ID NO:50 in the sequence listing) was added, and fluorescence in the cells was examined.

Figure 19:
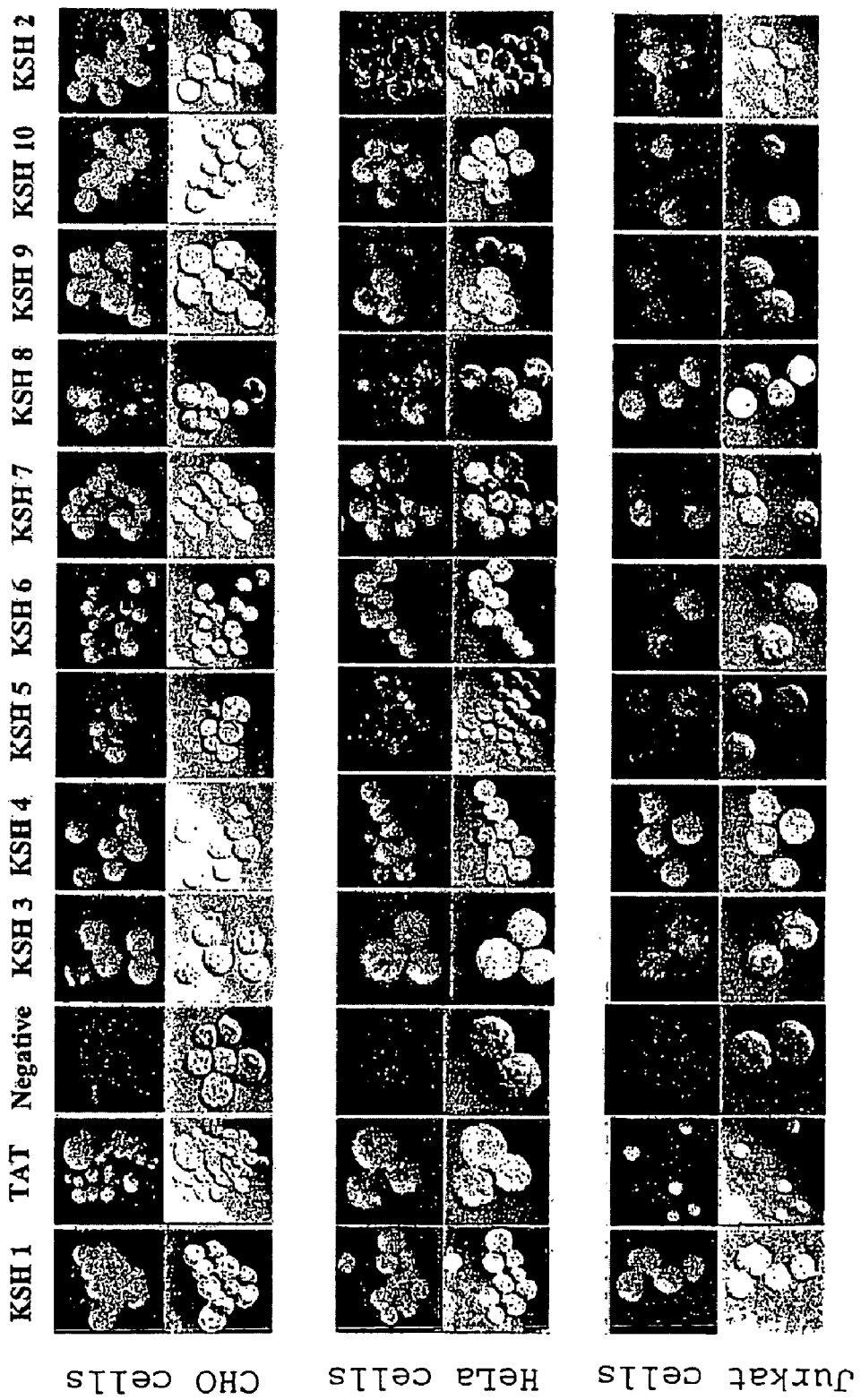
FIG. 19 A representation showing results of intracellular translocation tests with the addition of 25 µM of each fluorescence-labeled peptide. The upper panels show fluorescence from FITC; the lower panels show differential interference microscopic images of cells in combination with fluorescence images.

Regarding novel PTD sequence, each peptide was analyzed in a series of 2-fold dilutions at three levels from 50 µM to 12.5 µM. As a result, the results of the confocal microscopic analysis showed the same tendency as the results of the FACS analysis. For the four kinds of KSH2, KSH3, KSH4, KSH6, KSH7 and KSH10, the results of the confocal microscopic analysis, like the FACS analysis, revealed better intracellular translocation profiles than PTD1 (FIG. 19, the upper panels show the fluorescence of fluorescence-labeled peptides translocated into cells; the lower panels show differential interference microscopic images of cells in combination with fluorescence images; the peptide addition concentration was 25 µM). The PTD candidate sequences identified here clearly retained the capability of intracellular translocation. When database search was performed, no homologous sequences were observed; all were found to be novel PTD sequences. Regarding KSH2, the peptide was localized as fringing the surface of the cell membrane in HeLa cells, showing a transferability pattern different from that of other PTDs.

Example 5-3

Intracellular Translocation Test of Novel PTD Sequences and eGFP Fusion Proteins in CHO Cells For the six kinds of KSH2, KSH3, KSH4, KSH6, KSH7 and KSH10, eGFP fusion proteins were prepared, and whether the sequences had a PTD-like activity to translocation novel PTD sequences and eGFP fusion proteins into cells was determined. For the fusion proteins, molecular forms of high solubilization state were chosen. As a result, for KSH2 and KSH6, molecular type C in FIG. 14 was chosen, and for the remaining four kinds, type D in FIG. 14 was chosen. The fusion proteins were prepared in the same manner as Example 4-1. The annealing oligo-sequences used here are as shown in Table 3. Used for negative control was eGFP-His; after respective fluorescence intensities were uniformized, the respective fusion proteins were added to the CHO cells.

TABLE 5

| name of modified PTD peptide | forward oligomer (F) or reverse oligomer (R) | SEQ ID NO: in the sequence listing |
|---|---|---|
| KSH3 | F | 100 |
|  | R | 101 |
| KSH4 | F | 102 |
|  | R | 103 |
| KSH6 | F | 104 |
|  | R | 105 |
| KSH7 | F | 106 |
|  | R | 107 |
| KSH10 | F | 108 |
|  | R | 109 |
| KSH2 | F | 110 |
|  | R | 111 |

After incubation at 37° C. for 1 hour, trypsinization was performed, and the cells were recovered. After washing operation, the presence or absence of translocation into cells was determined using a confocal microscope. In performing a measurement, conditions were established under which fluorescence was not detected in CHO cells to which negative control eGFP-His had been added, after which measurements of cells to which each novel PTD fusion eGFP protein had been added were performed. As a result, fluorescence was observed in CHO cells to which any prepared novel PTD fusion eGFP protein had been added, demonstrating the translocation of the fusion proteins into cells.

From this finding, it was found that the above-described six kinds of novel PTD sequences had PTD-like activity. For the KSH7 peptide, basic amino acids shared by known PTDs that have been reported to date, such as arginine, were present alone, representing a new category of PTD. Of the six kinds of novel PTDs, KSH4 and KSH2 exhibited higher translocation into cells than the other novel PTDs and KSH1 peptide, and were useful when a protein, particularly eGFP, was used as the cargo.

Example 6

Intracellular Translocation Tests of Modified PTD Sequence Peptides of SEQ ID NO:47 in CHO Cells Example 6-1

Intracellular Translocation Test of Modified PTD Sequence Peptides Using a Confocal Microscope Of the novel PTD sequences found in Example 5, the KSH2 peptide is highly capable of translocating eGFP into cells; an attempt was made to modify the KSH2 peptide. The KSH2-1 to KSH2-4 peptides (SEQ ID NOS:44 to 47 in the sequence listing) were synthesized, fluorescently labeled, purified and dissolved in the same manner as Example 1-2, a test of translocation into CHO cells was performed, and confocal microscopic analysis was performed.

Figure 20:
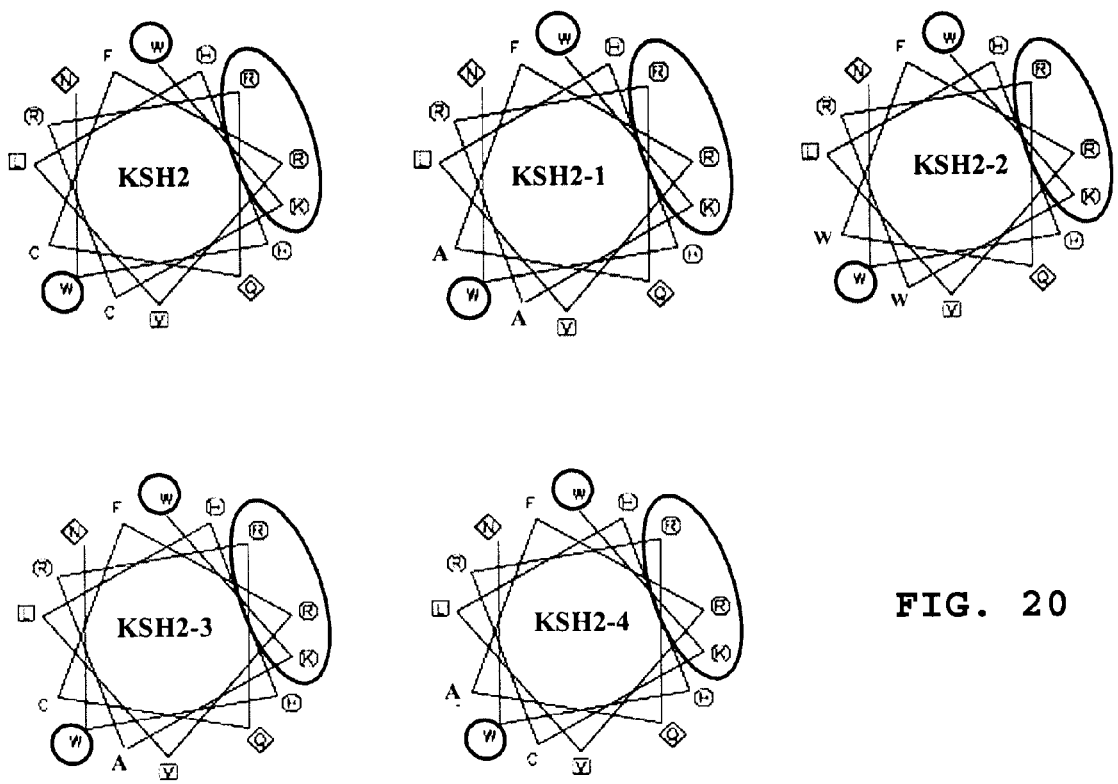
FIG. 20 A representation showing the wheel structures of the peptides KSH2 (SEQ ID NO: 4) and KSH2-1 to 2-4 (SEQ ID NOS: 44-47).

The KSH2 peptide is characterized by the formation of a lysine-arginine cluster on the wheel structure and the presence of two tryptophans. Another characteristic is that two cysteines are present as sandwiching tryptophan. From analyses that have been performed to date, it has been found that a basic amino acid cluster and tryptophan are important. Hence, in modifying the KSH2 peptide, the influence of substitution of the two cysteines with other amino acids was examined (FIG. 20).

Figure 21:
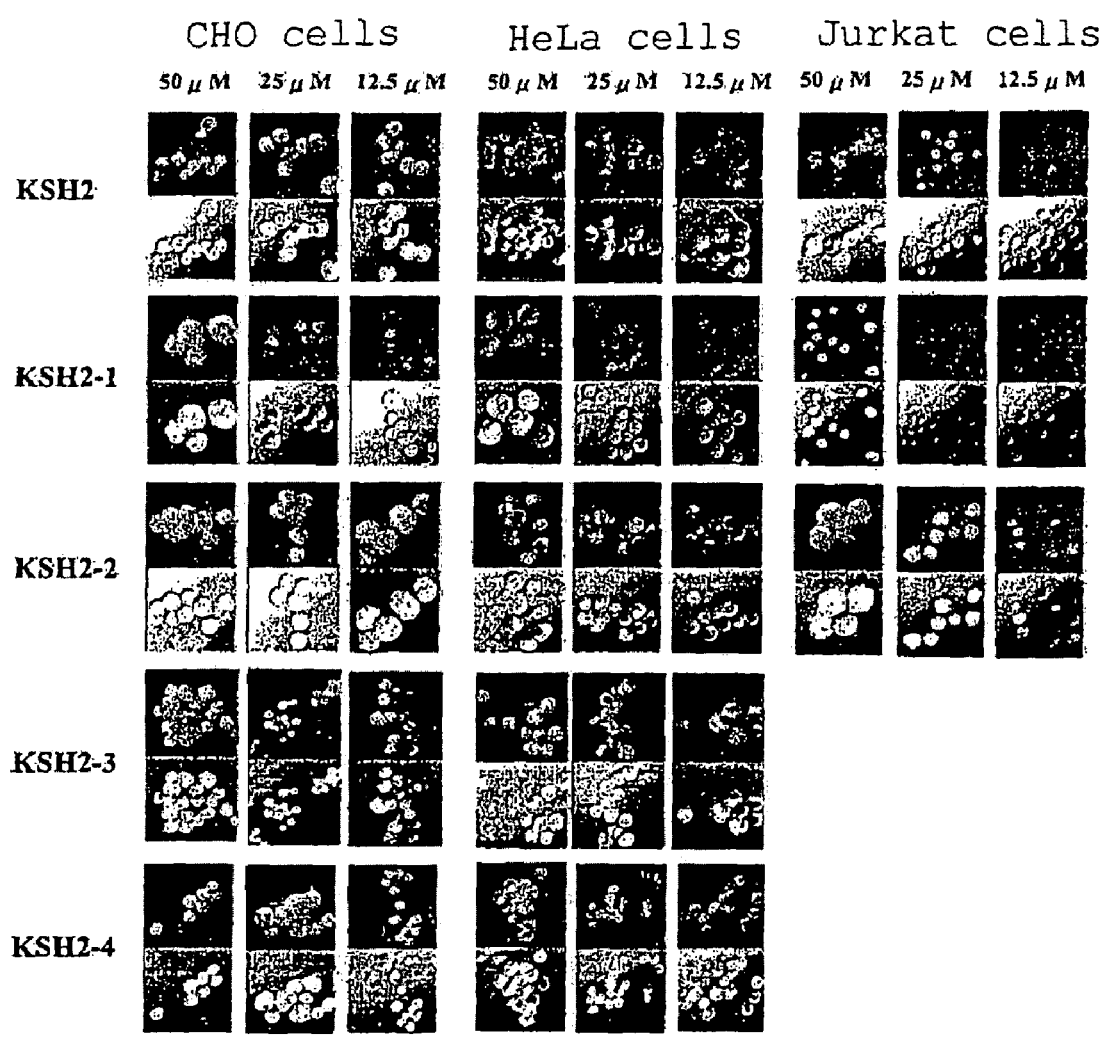
FIG. 21 A representation showing results of intracellular translocation tests with the addition of 50 µM, 25 µM and 12.5 µM of each fluorescence-labeled peptide. The upper panels show fluorescence from FITC; the lower panels show differential interference microscopic images of cells in combination with fluorescence images.

First, two cases were examined: two cysteines were substituted with alanine (KSH2-1) or with tryptophan (KSH2-2). FITC-labeled peptides were synthesized, and their intracellular translocation efficiencies were examined using CHO, HeLa, and Jurkat cells (FIG. 21, the peptide addition concentration was 50 μM, 25 μM or 12.5 μM).

As a result, at a concentration of 50 μM, both KSH2-1 and KSH2-2 exhibited higher intracellular translocation than KSH2; when diluted to 25 μM, KSH2-1 exhibited remarkably decreased intracellular translocation. Meanwhile, KSH2-2 exhibited higher intracellular translocation efficiency than KSH2 even when diluted to 25 μM and 12.5 μM. In KSH2-2, which exhibited promoted intracellular translocation, the number of tryptophans was 4. As the number of tryptophans increases, the intracellular translocation of a peptide is accentuated; however, since this was thought to be likely to cause insolubilization in preparing a fusion protein, two cysteines were substituted one by one with alanine (KSH2-3 and KSH2-4), and the intracellular translocation was examined. When the capability of intracellular translocation of FITC-labeled peptides in CHO, HeLa, and Jurkat cells was examined, it was found that in both cases, the capability of intracellular translocation was accentuated, compared with KSH2.

Example 6-2

Intracellular Translocation Test of Fusion Proteins of Modified PTD Sequences and eGFP in CHO Cells For KSH2-3 and KSH2-4 (SEQ ID NOS:46 and 47 in the sequence listing), eGFP fusion proteins were prepared, and the transferabilities of KSH2 and eGFP fusion proteins were compared in terms of PTD-like activity to translocation the novel PTD sequences and eGFP fusion proteins into cells. The fusion proteins prepared were type C in FIG. 14 for KSH2 and type D in FIG. 14 for KSH2-3 and KSH2-4. The fusion proteins were prepared in the same manner as Example 4-1. The annealing oligo-sequences used here are as shown in Table 4.

TABLE 6

| name of modified PTD peptide | forward oligomer (F) or reverse oligomer (R) | SEQ ID NO: in the sequence listing |
|---|---|---|
| KSH2-3 | F | 112 |
|  | R | 113 |
| KSH2-4 | F | 114 |
|  | R | 115 |

When the capability of translocation into CHO cells was examined, translocation into cells was confirmed for both fusion proteins of KSH2-3 and KSH2-4 with eGFP. Regarding intracellular translocation efficiency, the capability of translocation was lower than that of the eGFP fusion protein with the KSH2 peptide, but was equivalent to that of TAT-derived PTD1.

In summary, it was concluded that it is efficient to choose KSH2 when a polymeric protein is used as the cargo, and to choose the modified forms KSH2-3 and KSH2-4 when low-molecular substances like peptides are used.

INDUSTRIAL APPLICABILITY

According to the present invention, it is possible to provide a cell penetrating peptide having a novel amino acid sequence and a pharmaceutical containing the peptide. This application claims priority based on a Japanese patent application No. 2005-314355.

The invention claimed is:

1. An isolated peptide having the capability of translocation to cells, wherein said peptide comprises the amino acid sequence shown below:

B-X-Z-X-Arg-Z-Tyr-J-X-$O^1$-X-Arg-$O^2$-X-X or X-X-$O^1$-Arg-X-$O^2$-X-J-Tyr-Z-Arg-X-Z-X-B wherein
(i) B is arginine or lysine,
(ii) at least one of $O^1$ or $O^2$ is arginine, wherein, when one of $O^1$ or $O^2$ is arginine, the remaining $O^1$ or $O^2$ is an arbitrarily chosen amino acid,
(iii) Z is a hydrophobic amino acid,
(iv) J is serine or alanine, and
(v) X is an arbitrarily chosen amino acid;
with the proviso that when Z is leucine and $O^1$ is arginine, then J is alanine or B is lysine.

2. An isolated peptide having the capability of translocation to cells which is
(a) a peptide comprising the amino acid sequence of any one of SEQ ID NOS: 1, 2, 6-13, 15, 17-20, 22-30, 32 and 33 or the reversed-chain peptide thereof; or
(b) a peptide comprising the amino acid sequence of (a) above wherein one or two amino acids have been substituted, deleted, added or inserted.

3. An isolated peptide having the capability of translocation to cells, wherein said peptide is one of the following (a) or (b):

(a) a peptide comprising the amino acid sequence of any one of SEQ ID NOS: 3-5, 14, 16, 21, 31 and 35-47 or the reversed-chain peptide thereof;
(b) a peptide comprising the amino acid sequence of (a) above wherein one or two amino acids have been substituted, deleted, added or inserted.

4. An isolated peptide comprising the amino acid sequence of any one of SEQ ID NOS: 1 to 33 and 35-47 or the reversed-chain peptide thereof.

5. A peptide-bound bioactive substance comprising the isolated peptide of claim 1 and a bioactive substance, wherein said bioactive substance is bound to said peptide.

6. The peptide-bound bioactive substance of claim 5, wherein the bioactive substance is selected from the group consisting of a protein having a bioactivity, a polypeptide having a bioactivity, a liposome-encapsulated drug, a liposome-encapsulated polyethylene-glycolated drug, a low-molecular weight compound, a nucleic acid, a magnetic bead, a nano-gauge particle and a phage.

7. The peptide-bound bioactive substance of claim 6, wherein the protein having a bioactivity is an about 10 KDa to about 120 KDa protein, and wherein the polypeptide having a bioactivity has 4 to 30 amino acids.

8. An isolated cell or a non-human cell comprising the peptide-bound bioactive substance of claim 5.

9. An isolated nuclei or a non-human nuclei comprising the peptide-bound bioactive substance of claim 5.

10. A peptide-bound bioactive substance comprising the isolated peptide of claim 3 and a bioactive substance.

11. The peptide-bound bioactive substance of claim 10, wherein the bioactive substance is selected from the group consisting of a protein having a bioactivity, a polypeptide having a bioactivity, a liposome-encapsulated drug, a liposome-encapsulated polyethylene-glycolated drug, a low molecular weight compound, a nucleic acid, a magnetic bead, a nano-gauge particle and a phage.

12. The peptide-bound bioactive substance of claim 11, wherein the protein having a bioactivity is an about 10 KDa to about 120 KDa protein, and wherein the polypeptide having a bioactivity has 4 to 30 amino acids.

13. An isolated cell or a non-human cell comprising the peptide-bound bioactive substance of claim 10.

14. An isolated cell nucleus or a non-human cell nucleus comprising the peptide-bound bioactive substance of claim 10.

15. A method for delivering a bioactive substance into a cell and/or a cell nucleus in a mammal in need thereof that comprises administering to the mammal in need thereof an effective amount of a peptide-bound bioactive substance comprising the isolated peptide of claim 1 and the bioactive substance, wherein said bioactive substance is bound to said peptide.

16. The method of claim 15, wherein the bioactive substance is an anti-allergic drug.

17. A method for delivering a bioactive substance into a cell and/or a cell nucleus in a mammal in need thereof, which comprises administering to the mammal in need thereof an effective amount of a peptide-bound bioactive substance comprising the isolated peptide of claim 3 and the bioactive substance, wherein said bioactive substance is bound to said peptide.

18. The method of claim 17, wherein the bioactive substance is an anti-allergic drug.

19. The isolated peptide of claim 2, wherein said peptide has the sequence of:
 (a) a peptide comprising the amino acid sequence of any one of SEQ ID NOS: 1, 2, 6-13, 15, 17-20, 22-30 and 32-33 or the reversed-chain peptide thereof.

20. The isolated peptide of claim 2, wherein said peptide has the sequence of:
 (b) a peptide comprising the amino acid sequence of any one of SEQ ID NOS: 1, 2, 6-13, 15, 17-20, 22-30 and 32-33 or the reversed-chain peptide thereof wherein one or two amino acids have been substituted, deleted, added or inserted.

21. The isolated peptide of claim 3, wherein said peptide has the sequence of:
 (a) a peptide comprising the amino acid sequence of any one of SEQ ID NOS: 3-5, 14, 16, 21, 31 and 35-47 or the reversed-chain peptide thereof.

22. The isolated peptide of claim 3, wherein said peptide has the sequence of:
 (b) a peptide comprising the amino acid sequence of any one of SEQ ID NOS: 3-5, 14, 16, 21, 31 and 35-47 or the reversed-chain peptide thereof wherein one or two amino acids have been substituted, deleted, added or inserted.

23. An isolated D-form peptide having the capability of translocation to cells, wherein said peptide comprises the amino acid sequence shown below:
 (a) B-X-Z-X-Arg-Z-Tyr-J-X-$O^1$-X-Arg-$O^2$-X-X or X-X-$O^1$-Arg-X-$O^2$-X-J-Tyr-Z-Arg-X-Z-X-B
 wherein
 (i) B is arginine or lysine,
 (ii) at least one of $O^1$ or $O^2$ is arginine, wherein, when one of $O^1$ or $O^2$ is arginine, the remaining $O^1$ or $O^2$ is an arbitrarily chosen amino acid,
 (iii) Z is a hydrophobic amino acid,
 (iv) J is serine or alanine, and
 (v) X is an arbitrarily chosen amino acid; or
 (b) the amino acid sequence of (a) above wherein one or two amino acids have been substituted, deleted, added or inserted.

24. The isolated D-form peptide of claim 23, which comprises B-X-Z-X-Arg-Z-Tyr-J-X-$O^1$-X-Arg-$O^2$-X-X.

25. The isolated D-form peptide of claim 23, which comprises X-X-$O^1$-Arg-X-$O^2$-X-J-Tyr-Z-Arg-X-Z-X-B.

26. The isolated D-form peptide of claim 23, which is
 (a) a peptide comprising the amino acid sequence of any one of SEQ ID NOS: 1, 2, 6-13, 15, 17-20, 22-30, 32 and 33 or the reversed-chain peptide thereof; or
 (b) a peptide comprising the amino acid sequence of (a) above wherein one or two amino acids have been substituted, deleted, added or inserted.

27. The isolated D-form peptide of claim 26 which comprises any one of SEQ ID NOS: 1, 2, 6-13, 15, 17-20, 22-30, 32 or 33.

28. The isolated D-form peptide of claim 26 which comprises any one of a reverse-chain peptide of SEQ ID NOS: 1, 2, 6-13, 15, 17-20, 22-30, 32 or 33.

29. A D-form of an isolated peptide that comprises any one of SEQ ID NOS: 1-33 or 35-47 or a reversed chain peptide thereof.

30. A peptide-bound bioactive substance comprising the isolated D-form peptide of claim 26 and a bioactive substance, wherein said bioactive substance is bound to said peptide.

31. A method for delivering a bioactive substance into a cell and/or a cell nucleus in a mammal in need thereof, which comprises administering to the mammal in need thereof an effective amount of a peptide-bound bioactive substance comprising the isolated D-form peptide of claim 26 and the bioactive substance, wherein said bioactive substance is bound to said peptide.

* * * * *